United States Patent [19]

Lauffer et al.

[11] Patent Number: 5,306,718
[45] Date of Patent: Apr. 26, 1994

[54] OXIME AND AMINE SUBSTITUTED AZABICYCLO AND AZOCYCLO MUSCARINIC AGONISTS AND METHODS OF TREATMENT

[75] Inventors: David J. Lauffer, Saline, Mich.; Walter H. Moos, Emeryville, Calif.; Michael R. Pavia, Ann Arbor, Mich.; Haile Tecle, Ypsilanti, Mich.; Anthony J. Thomas, Ann Arbor, Mich.

[73] Assignee: Warner-Lambert Company, Morris Plains, N.J.

[21] Appl. No.: 778,412

[22] Filed: Oct. 16, 1991

Related U.S. Application Data

[63] Continuation-in-part of Ser. No. 641,478, Jan. 22, 1991, abandoned, which is a continuation-in-part of Ser. No. 591,647, Oct. 2, 1990, abandoned, which is a continuation-in-part of Ser. No. 488,916, Mar. 6, 1990, abandoned.

[51] Int. Cl.$^5$ .............. C07D 211/72; A61K 31/00
[52] U.S. Cl. .............. 514/230.8; 514/231.5; 514/241; 514/255; 514/256; 514/269; 514/315; 544/125; 544/216; 544/238; 544/298; 544/315; 544/362; 546/242; 546/243; 546/244
[58] Field of Search .............. 546/242, 243, 244; 514/315, 230.8, 231.5, 241, 255, 256, 269; 544/125, 216, 238, 298, 315, 362

[56] References Cited

U.S. PATENT DOCUMENTS

| | | | |
|---|---|---|---|
| 3,371,094 | 2/1968 | Zenitz et al. | 546/244 |
| 3,502,692 | 3/1970 | Feldman et al. | 546/244 |
| 4,104,251 | 8/1978 | Wiezer et al. | 546/244 |
| 4,341,795 | 7/1982 | Liang | 546/244 |
| 4,710,508 | 12/1987 | Bergmeier et al. | 514/357 |

FOREIGN PATENT DOCUMENTS 2086292 12/1971 France.
46-024370 7/1971 Japan.

OTHER PUBLICATIONS

*The Lancet*, vol. 2:1403, (1976), Davies et al., "Selective Loss of Central Cholinergic Neurons in Alzheimer's Disease".

(List continued on next page.)

*Primary Examiner*—Marianne M. Cintins
*Assistant Examiner*—Catherine Scalzo
*Attorney, Agent, or Firm*—Michael J. Atkins

[57] ABSTRACT

Pharmaceutically useful nitrogen containing cyclic oxime and amine substituted compounds of the following general Formulas I, II and III are disclosed:

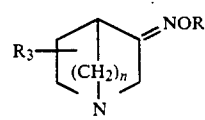

Ia

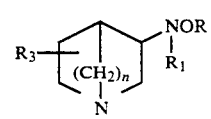

IIb

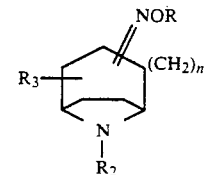

IIIc

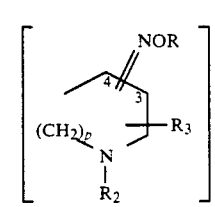

IVd

Specifically the compounds are azabicyclo [2.2.1] omimes, azabicyclo [2.2.2] oximes, azabicyclo [2.2.1] amines, azabicyclo [2.2.2] amines, azabicyclo [3.2.1] oximes and amine containing heterocyclic oximes wherein the heterocyclic ring contains from 4 to 5 [3 to 7] carbon atoms.

21 Claims, No Drawings

OTHER PUBLICATIONS

*Journal of Neurological Sciences*, 34:247–265 (1977), Perry et al., "Neurotransmitter Enzyme Abnormalities in Senile Dementia".

*The Lancet*, vol. 1:668–670 (1977), White et al., "Neocortical Cholinergic Neurons in Elderly People".

*Neurobiology of Aging*, 4:25–30 (1983), Peterson et al., "Amelioration of Age-Related Neurochemical and Behavorial Deficits by 3,4-Diaminopyridine".

*Experimental Aging Research*, vol. 9, No. 3:211–214 (1983), Davis et al. "Improvement of 8-Arm Maze Performance in Aged Fischer 344 Rats . . . ".

*Brit. J. Psychiat.*, 138:46–50 (1981), Christie et al., "Physostigmine and Arecoline: Effects of Intravenous in Alzheimer Presenile Dem".

Dissertation Abstract Int., B, 1984 45, (7), 2120; CA 102:113440m.

Chemical Abstracts Service: CA75:129542f (1971).

OXIME AND AMINE SUBSTITUTED AZABICYCLO AND AZOCYCLO MUSCARINIC AGONISTS AND METHODS OF TREATMENT

RELATIONSHIP TO OTHER APPLICATIONS

This application is a continuation-in-part of copending U.S. patent application Ser. No. 07/641,478, filed on Jan. 22, 1991, now abandoned is a continuation-in-part of copending U.S. patent application Ser. No. 07/591,647, filed Oct. 2, 1990, now abandoned, which is a continuation-in-part of copending U.S. patent application Ser. No. 07/488,916, filed Mar. 6, 1990, now abandoned.

FIELD OF INVENTION

The present invention is a class of oximes and amines which are muscarinic agonists, rendering them useful as pharmaceutical agents. More specifically, the compounds are azabicyclic and azacyclic oximes and amines.

BACKGROUND

Disorders of cognition are generally characterized by symptoms of forgetfulness, confusion, memory loss, attentional deficits, and/or, in some cases, affective disturbances. These symptoms may arise as a result of the general aging process and/or from organic brain disease, cerebrovascular disease, head injury, or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over 60 years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia, for example, the level of the enzyme choline acetyltransferase (CAT) can be reduced by as much as 90%. (See Davies, et al, *The Lancet,* 1976 (Vol. 2):1403; Perry, et al, *J. Neurol. Sci.,* 34:247-265 (1977); and White, et al, *The Lancet,* 1977 (Vol. 1):668-670).

Since CAT catalyzes the synthesis of acetylcholine from its precursors choline and acetyl coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory formation.

The cholinergic hypothesis suggests that drugs which restore acetylcholine levels or which mimic the action of acetylcholine (i.e., are cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction. (See C. Peterson and G. E. Gibson, *Neurobiol. Aging,* 4:25-30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine. (See H. P. Davis, et al, *Exp. Aging Res.,* 9:211-214 (1983)).

It has been known for some time that the natural alkaloid, muscarine, has the ability to act relatively selectively at autonomic effector cells to produce qualitatively the same effects as acetylcholine. Two alkaloids, pilocarpine and arecoline (the methyl ester of 1,2,5,6-tetrahydro-1-methyl-3-pyridinecarboxylic acid), have the same principal sites of action as muscarine and acetylcholine and are thus classified as having "muscarinic" action. Although these naturally occurring alkaloids are of great value as pharmacological tools, present clinical use is largely restricted to the use of pilocarpine as miotic agent.

Recently it has been demonstrated that arecoline is effective in ameliorating some of the symptoms of cognitive disorders in patients clinically diagnosed as having presenile primary degenerative dementia. Significant improvement was observed in a test of picture recognition after administration of arecoline to patients in a double-blind study. (See Christie, et al, *Brit. J. Psychiatry,* 138:46-50 (1981)).

INFORMATION DISCLOSURE STATEMENT

Certain 3- or 4-ketoximes of 1-(lower alkyl)-1,2,5,6-tetrahydropyridines in which the oxygen is unsubstituted are disclosed in U.S. Pat. No. 3,004,979, having utility as parasympathomimetic agents acting on nonstriated muscle.

U.S. Pat. No. 4,710,508 describes O-substituted 1-(1,2,3,6-tetrahydro-1-methyl-3-pyridinyl)ketone oximes and O-substituted 1-(1,2,3,6-tetrahydro-4-pyridinyl)ketone oximes which are useful as analgesic agents or agents for the treatment of the symptoms of cerebral insufficiency characterized by decreased central acetylcholine production.

Dissertation Abstracts Int. B 1984, 45(7), 2120; CA102:113440 m describes oxime-O-ethers of the following formula as having anticholinergic properties:

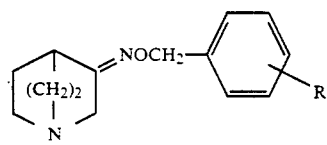

wherein R is F, Cl, Br, $NO_2$, $OCH_3$, $CF_3$, or $CH_3$. Particularly relevant are pages 128-136, 166, 167, 198-203.

French 2,086.292 describes 3-quinuclidinone oxime carbamates of the following formula having insecticidal and acaricidal activity.

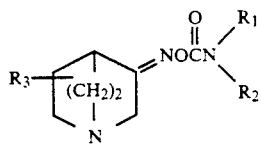

wherein $R_3$ is alkyl, alkenyl, alkylidene, halogen, cyano, haloalkyl, haloalkenyl, alkoxy, etc; $R_1$ and $R_2$ are hydrogen, lower alkyl, acyl which may be substituted, lower alkenyl, or the group R—O—CH$_2$—wherein R is methyl, ethyl, isopropyl; propyl- 1,2-diene, allyl, 1-methyl-2-propenyl; phenyl or benzyl.

SUMMARY OF THE INVENTION

The present invention is directed to compounds of the following general Formulas I, II, III, and IV and pharmaceutically acceptable salts thereof.

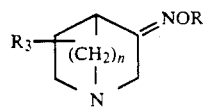
Ia

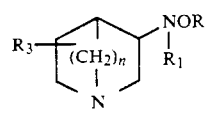
IIb

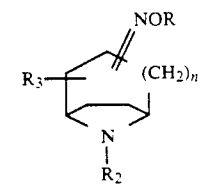
IIIc

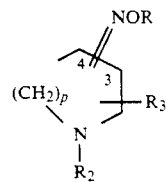
IVd wherein n is one or two; wherein p is zero or one to four, wherein each of $R_1$ and $R_2$ is hydrogen or straight or branched lower alkyl having from 1 to 4 carbon atoms; wherein $R_3$ is hydrogen, a straight or branched lower alkyl group having from 1 to 6 carbon atoms, or cycloalkyl having from 3 to 6 carbon atoms, hydroxy, a straight or branched lower alkoxy group having from 1 to 4 carbon atoms, an acyloxy group wherein the acyl moiety has from 2 to 5 carbon atoms or the group —(CH$_2$)$_q$NR$_{11}$R$_{12}$ wherein q is zero or one to four and each of $R_{11}$ and $R_{12}$ is the same or different and is hydrogen or a straight or branched lower alkyl group having from 1 to 4 carbon atoms; wherein R is hydrogen or the group:

—Y—Z wherein Y is a bond or a straight or branched hydrocarbon chain having from 1 to 20 carbon atoms and optionally contains from 1 to 4 double and/or triple bonds; and Z is hydrogen;

a cycloalkyl group having from 3 to 6 carbon atoms;

an aromatic group selected from phenoxy, phenyl, 2- or 3-thienyl, 2- or 3-furanyl, 2- or 3-pyrrolyl, 2-, 3-, or 4-pyridinyl wherein the aromatic group is unsubstituted or is substituted with 1 or 2 substituents selected from straight or branched alkyl having from 1 to 4 carbon atoms, straight or branched alkoxy having from 1 to 4 carbon atoms, chlorine, bromine, fluorine, trifluoromethyl, nitro, hydroxy, trifluoromethoxy, amino, amino substituted with 1 or 2 straight or branched lower alkyl groups having from 1 to 4 carbon atoms;

—NR$_6$R$_7$ wherein R$_6$ and R$_7$ are the same or different and are hydrogen, straight or branched alkyl having from 1 to 4 carbon atoms, phenyl, benzyl, or —NR$_6$R$_7$ taken together form a pyrrolidino, piperidino, piperazino, or morpholino ring;

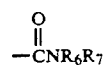

wherein each of R$_6$ and R$_7$ has the meaning defined above;

wherein R$_8$ is a straight or branched alkyl group having from 1 to 6 carbon atoms; —CN; —CO$_2$R$_9$ wherein R$_9$ is hydrogen, a straight or branched hydrocarbon group having from 1 to 6 carbon atoms and which is saturated or is unsaturated containing 1 or 2 double and/or triple bonds, or benzyl;

—XR$_{10}$ wherein X is oxygen or sulfur and R$_{10}$ is a straight or branched hydrocarbon chain having from 1 to 6 carbon atoms and which optionally contains 1 or 2 double or triple bonds and is unsubstituted or is substituted with an alkoxy group having from 1 to 4 carbon atoms;

with that the following compounds are excluded: (a) compounds of Formula I wherein n is two, and R is hydrogen, or the group Y-Z wherein Y is a bond and Z is —C(=O)NR$_6$R$_7$ or —C(=O)R$_8$; and (b) compounds of Formulas III and IV wherein R is hydrogen.

Pharmaceutical compositions comprising compounds of Formulas I, II, III, or IV are also included in the present invention as well as methods of using the compounds as analgesics and in the treatment of cognitive decline. The geometric isomers and their optical isomers and pharmaceutically acceptable salts of the compounds of Formula I are also included within the scope of the present invention.

The compounds of the present invention may further be described as follows being compounds of the following Formulas I, II, III, or IV, and their enantiomers, or a pharmaceutically acceptable salt thereof:

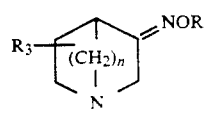
I

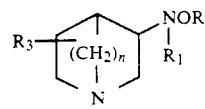
II

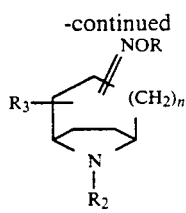

III

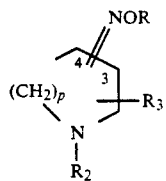

IV wherein n is one or two;
wherein p is zero or one to four;
wherein each of $R_1$ and $R_2$ is hydrogen or straight or branched lower alkyl having from 1 to 4 carbon atoms;
wherein $R_3$ is hydrogen, a straight or branched lower alkyl group having from 1 to 6 carbon atoms, hydroxy, a straight or branched lower alkoxy group having from 1 to 4 carbon atoms, acyloxy group wherein the acyl moiety has from 2 to 5 carbon atoms, or the group —$(CH_2)_qNR_{11}R_{12}$ wherein q is zero or 1 to 4 and each or $R_{11}$ and $R_{12}$ is the same or different and is hydrogen or a straight or branched lower alkyl group having from 1 to 4 carbon atoms; or cycloalkyl having from 3 to 6 carbon atoms;
wherein R is
(a) hydrogen;
(b) a straight or branched hydrocarbon chain having from 1 to 20 carbon atoms which is saturated or which is unsaturated and contains from 1 to 4 double and/or triple bonds;
(c) phenyl or phenyl substituted with 1 to 3 substituents selected from chlorine, bromine, fluorine, trifluoromethyl, hydroxy, trifluoromethoxy, straight or branched alkoxy having from 1 to 4 carbon atoms, straight or branched alkyl having from 1 to 4 carbon atoms, nitro, —$NR_4R_5$ wherein each of $R_4$ and $R_5$ is hydrogen or a straight or branched alkyl group having from 1 to 4 carbon atoms;
(d) cycloalkyl having from 3 to 8 carbon atoms or a cycloalkenyl group having from 4 to 8 carbon atoms;
(e) a straight or branched hydrocarbon chain having from 1 to 20 carbon atoms which is saturated or which is unsaturated and contains 1 to 4 double and/or triple bonds, and the terminal carbon of the hydrocarbon chain is substituted with a group selected from:
(i) a cycloalkyl group having from 3 to 8 carbon atoms or a cycloalkenyl group having from 4 to 8 carbon atoms;
(ii) an aromatic group selected from phenoxy, phenyl, 2- or 3-thienyl, 2- or 3-furanyl, 2- or 3-pyrrolyl, 2-, 3-, or 4-pyridinyl, 3- or 5-(1,2,4)-thiadiazolyl, 3-(1,2,5)-thiadiazolyl, 2-(1,3,4)-thiadiazolyl, 2-triazinyl, 3-or 5-(1,2,4)-oxadiazolyl, 2-(1,3,4)-oxadiazolyl, 3-(1,2,5)-oxadiazolyl, 3-or 5-thiadiazolyl, 2- or 5-pyrimidinyl, 3- or 4-pyridazinyl, 2-, 4-, or 5-thiazolyl, 2-, 4-, or 5-oxazolyl, or 2-pyrazinyl wherein the aromatic group is unsubstituted or is substituted with 1 or 2 substituents selected from straight or branched alkyl having from 1 to 4 carbon atoms, straight or branched alkoxy having from 1 to 4 carbon atoms, chlorine, fluorine, bromine, trifluoromethyl, nitro, hydroxy, trifluoromethoxy, or $NR_4R_5$ wherein $R_4$ and $R_5$ have the meanings defined above,
(iii) —$NR_6R_7$
wherein each of $R_6$ and $R_7$ is hydrogen, alkyl having from 1 to 4 carbon atoms, phenyl or benzyl, or —$NR_6R_7$ taken together form a pyrrolidino, piperidino, piperazino, or morpholino ring;
(iv)

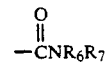

wherein $R_6$ and $R_7$ have the meanings defined above;
(v)

wherein $R_8$ is a straight or branched alkyl group having from 1 to 6 carbon atoms;
(vi) CN;
(vii) —$CO_2R_9$
wherein $R_9$ is hydrogen, a straight or branched hydrocarbon group having from 1 to 6 carbon atoms which is saturated or which is unsaturated and contains 1 or 2 double and/or triple bonds, or benzyl;
(viii) $XR_{10}$
wherein X is oxygen or sulfur, and $R_{10}$ is a straight or branched hydrocarbon chain having from 1 to 6 carbon atoms which is saturated or which is unsaturated and contains 1 or 2 double and/or triple bonds and is unsubstituted or is substituted with an alkoxy group having from 1 to 4 carbon atoms;
(ix) biphenylyl;
(f) the group —$CH_2CH_2CH=C(Ph)_2$; or
(g) the group

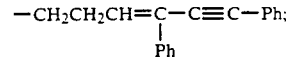

the individual isomers as enantiomers and geometric isomers and pharmaceutically acceptable salts;
with the proviso that the following compounds are excluded:
(a) compounds of Formula I wherein n is two, and R is hydrogen, —C(=O)$NR_6R_7$ or —C(=O)$R_8$; and
(b) compounds of Formulas III and IV wherein R is hydrogen.

DETAILED DESCRIPTION OF THE INVENTION

In the compounds depicted by general Formulas I, II, III, and IV the various substituents are further described as follows. Illustrative examples of straight or branched lower alkyl having from 1 to 4 carbon atoms or from 1 to 6 carbon atoms included methyl, ethyl, n-propyl, isopropyl, n-butyl, tert-butyl, n-pentyl, n-hexyl.

Illustrative of lower alkoxy groups having from 1 to 4 carbon atoms are methoxy, ethoxy, and n-propoxy.

Illustrative examples of a saturated straight or branched hydrocarbon chain having from 1 to 20 carbon atoms include n-octyl, n-heptyl, dodecyl, tetradecyl, heptadecyl, etc, and all the illustrative examples of straight or branched lower alkyl groups having from 1 to 6 carbon atoms set forth above.

Illustrative examples of straight or branched unsaturated hydrocarbon chains which contain from 1 to 4 unsaturations which are double or triple bonds are ethenyl, 2,4-pentadienyl, 1,4-pentadienyl, 2,4-pentadiynyl, 1,4-pentadiynyl, 2-penten-4-ynyl, 2-pentyn-4-enyl, 2-propenyl, 3-butenyl, 1-methyl-2-propenyl, 2-pentenyl, 2-octenyl, 5-nonenyl, 4-undecenyl, 2-ethyl-3-butenyl, 4-hexenyl, 9,12-octadienyl, hexadecenyl, ethynyl, 2-propynyl, 1-methyl-2-propynyl, 1-ethyl-2-propynyl, 1-methyl-3-butynyl, 3-butynyl, or 4-pentynyl. Illustrative examples of cycloalkyl groups having from 3 to 6 carbon atoms are cyclopropyl, cyclobutyl, and cyclohexyl.

Pharmaceutically acceptable acid addition salts of the compounds of Formulas I, II, III, and IV are illustratively hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane- and hydroxyethanesulfonic. (See, for example, "Pharmaceutical Salts," *J. Pharm. Sci.* 66(1):1-19 (1977).

Preferred compounds of the present invention are those of Formulas I and III with the compounds of Formula I being more preferred. The most preferred compounds of this invention are those of Formula I wherein n is one, i.e., compounds of the following Formula V:

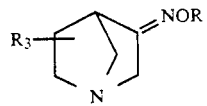
V

In general Formula V, R, and $R_3$ have the same meanings as set forth above for Formulas I, II, III, and IV. Compounds of Formula V wherein $R_3$ is hydrogen and R is other than hydrogen or is other than group (e) wherein the terminal carbon substituent is group (iv) are more preferred. Most particularly preferred are compounds wherein R is a straight or branched hydrocarbon chain having from 1 to 9 carbon atoms wherein the terminal carbon atom is unsubstituted or is substituted with group (ii) as defined above. Illustrative of the most preferred hydrocarbon groups which R may represent are the following: $CH_3$; $-CH_2C\equiv C-Q$; $-CH_2C\equiv CCH_2C\equiv C-Q$; $-CH_2\equiv CCH_2C\equiv CCH_2C\equiv C-Q$; and

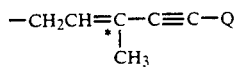

where * means the stereoconfiguration may be E or Z and wherein Q is hydrogen or has the definition set forth at (e)(ii) for group R. Most preferably, Q is hydrogen, phenyl, or substituted phenyl.

Compounds of Formula I wherein n is two may be depicted as set forth below in Formula VI:

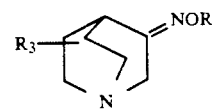
VI wherein R and $R_3$ have the meanings defined above.

Compounds of Formula II wherein n is one may be depicted as set forth below in Formula VII and wherein n is two may be depicted as set forth below in Formula VIII:

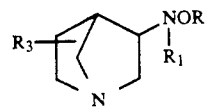
VII

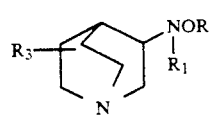
VIII

In Formulas VII and VIII the substituent groups represented by $R_3$, R, and $R_1$ have the meanings defined hereinabove in Formulas I, II, III, and IV.

In the compounds of Formulas III and Iv the =NOR group is attached to either the 2-, 3-, or 4-position (Formula III) or the 3- or 4-position (Formula IV) of the ring.

In addition to the novel compounds of the present invention as represented by Formulas I through VIII above, the present invention provides novel pharmaceutical preparations.

The present invention provides pharmaceutical compositions useful as analgesic agents comprising an analgesically effective amount of a compound as defined above in combination with a pharmaceutically acceptable carrier. In another aspect, the present invention provides a method of alleviating pain in a mammal comprising administering to a mammal in need of such treatment an analgesically effective amount of a compound as defined above in combination with a pharmaceutically acceptable carrier.

In another aspect, the present invention provides pharmaceutical compositions for treating the symptoms of senile cognitive decline comprising a cholinergically effective amount of a compound as defined above in combination with a pharmaceutically acceptable carrier. In yet another aspect, the present invention provides a method of treating the symptoms of senile cognitive decline in the elderly characterized by decreased cerebral acetylcholine production or release comprising administering to a patient in need of such treatment of cholinergically effective amount of a compound as defined above in combination with a pharmaceutically acceptable carrier.

The compounds of the present invention may exist in either of two Z and E isomeric and enantiomeric forms. The present invention includes both forms of the compounds as well as mixtures of the Z and E forms. Illustratively Formulas IX and X depict the Z and E forms of the compounds of Formula I. Moreover, in those compounds in which there is a double bond in a carbon chain, both the Z and E forms of the olefins are included in the present invention.

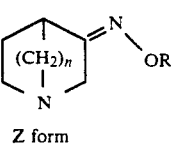

Z form

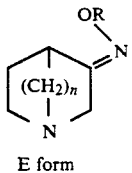

E form

The compounds of Formulas I, III, and IV are prepared by reacting a ketone of the following Formulas XI, XII, and XIII with an amine of the formula $NH_2OR \cdot HCl$ wherein R and $R_3$ have the meanings defined in Formulas I, II, III, and IV as depicted below:

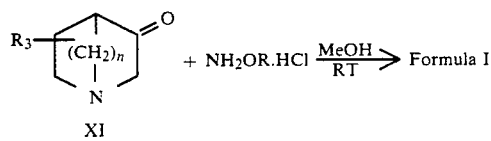

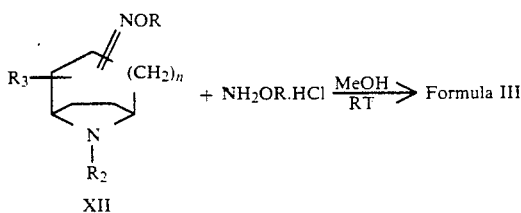

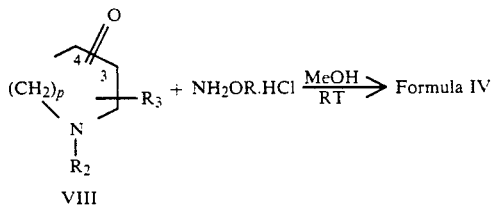

In each of the above depicted reactions, typically methanol is used as the solvent and the reaction is carried out at room temperature.

The compounds of Formula II are prepared by reducing Formula I compounds by procedures well known in the art, for example, by treatment with sodium cyanoborohydride under controlled pH conditions. Therefore, not only are the compounds of Formula I pharmaceutically useful they are also useful as starting material to make pharmaceutically useful compounds. Similarly, the compounds of Formula I wherein R is hydrogen may be used to prepare compounds of Formula I wherein R is the group —C(=O)R_6.

The salts are prepared by contacting the free base form of the compounds of this invention with a sufficient amount of the desired acid to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate maybe utilized for this purpose.

The free base forms of the compounds of this invention differ somewhat from their respective salt forms in such physical properties as melting point and solubility in polar solvents, but the salts are otherwise equivalent to their respective free acid or base forms for the purposes of the invention.

The starting materials represented by Formulas XI, XII, and XIII are known in the art or can be prepared by procedures generally known in the art. See, for example, J. Saunders, et al, *J. Chem. Soc., Chem. Comm.* 1988, 1618 and R. J. Snow and L. J. Street, *Tet. Lett.* 1989, 30, 5795. Also, the amines represented by $NH_2OR$ are commercially available or may be prepared by procedures generally known in the art. For example, the amines can be prepared by the Mitsunabu reaction by reacting a phthalimide with an appropriate alcohol and hydrolyzing the resultant intermediate using methylhydrazine. Similarly, the phthalimide can be reacted with an appropriate aliphatic or alicyclic bromide. The examples and preparations set forth below illustrate the synthesis of the compound of this invention.

EXAMPLE 1

1-Azabicyclo2.2.1]hept-3-one oxime hydrochloride

1-Azabicyclo[2.2.1]hept-3-one was prepared by the procedure described in *J. Chem. Soc., Chem. Comm.* 1988, 1618.

1-Azabicyclo[2.2.1]hept-3-one (2 g, 18 mmol) and hydroxlamine hydrochloride (1.25 g, 18 mmol) was dissolved in 10 mL MeOH and stirred at room temperature for 18 hours. The reaction mixture was concentrated in vacuo. The crystalline residue was recrystallized from ethanol to afford 2.04 g (70%) of the title product, m.p. 211° C.

$C_6H_{11}ClN_2O$: Calc.: C, 44.31; H, 6.82; N, 17.23.
Found: C, 44.25; H, 6.64; N, 17.18.
Mass Spec.: m/e 126.1 (M+for free base)
$^1$H NMR: δ (CDCl$_3$) 0.87 (1H, m), 1.31–1.46 (1H, m), 2.39–2.57 (5H, m), 3.01–3.21 (2H, m), 10.15 (1H, s), 10.58–10.82 (1H, br s). $^{13}$C NMR δ (CDCl$_3$) 25.2, 40, 50.5, 54.5, 58.5, 153.5

EXAMPLE 2

1-Azabicyclo[2.2.11hept-3-one, O-ethyloxime hydrochloride

1-Azabicyclo[2.2.1]hept-3-one (2 g, 18 mmol) was dissolved in 25 mL of methanol. Ethoxyamine hydrochloride (1.76 g, 18 mmol) was added and the reaction was stirred at room temperature for 18½ hours. The reaction was concentrated in vacuo to afford a yellow solid. The residue was dissolved in water, basified with saturated aqueous potassium carbonate, and extracted with dichloromethane (3×150 mL). The combined extracts were dried over anhydrous sodium sulfate and concentrated in vacuo to afford a clear, yellow liquid. The liquid was dissolved in diethyl ether and filtered through Celite. The filtrate was treated with ethereal hydrogen chloride to yield 2.5 g (75%) of the title product, m.p. 158°–160° C. $C_8H_{15}ClN_2O$: Calc.: C, 50.39; H, 7.93; N, 14.69.
Found: C, 49.96; H, 7.76; N, 14.56.
Mass Spec.: m/e 154.1 (M+for free base)
$^1$H NMR: δ (CDCl$_3$) 1.20–1.28 (3H, t), 1.97–2.05 (1H, m), 240–253 (1H, m), 3.29–3.42 (2H, m), 3.52–3.62 (2H, m), 3.83-3.95 (2H, m), 4.06-4.14 (2H, q), 4.20-4.27 (1H, m). $^{13}$C NMR: δ (CDCl$_3$) 14.4, 26.1, 40, 51.7, 55.8, 59.6, 70.3, 153.1.

EXAMPLE 3

1-Azabicyclo[2.2.1]hept-3-one, O-methyloxime hydrochloride

1-Azabicyclo[2.2.1]hept-3-one (1.9 g, 17.1 mmol) was dissolved in 10 mL of methanol. Methoxyamine hydrochloride (1.4 g, 17.1 mmol) was added and the reaction was stirred at room temperature for 18 hours. The reaction was concentrated in vacuo to afford a white solid. Recrystallization of the residue from ethanol-diisopropyl ether afforded 2.27 g (75%) of the title product as a mixture of Z and E isomers, m.p. 210°-211° C.

$C_7H_{13}ClN_2O$: Calc.: C, 47.59; H, 7.42; N, 15.86.
Found: C, 47.46; H, 7.54; N, 15.84
Mass Spec.: m/e 140.1 (M+ for free base).
$^1$H NMR: δ (CDCl$_3$) 1.99 (1H, m), 2.36-2.52 (1H, m), 3.37-3.65 (4H, m), 3.86, 3.88 (3H, 2s) (3H, s), 3.89-4.00 (2H, m), 4.21-4.29 (1H, m). $^{13}$C NMR: δ (CDCl$_3$) 25, 26, 37.2, 40, 51.5, 51.7, 55.7, 56.5, 59.0, 59.6, 62.3, 153, 153.5.

The above procedure was utilized for the synthesis of the products listed in Table 1.

TABLE 1

| Hydroxylamine.HCl | Product | Example No. |
|---|---|---|
| NH$_2$OCH$_2$C≡CH | 1-Azabicyclo[2.2.1]-heptan-3-one, O-(2-propynyl)oxime hydrochloride, m.p. 203° C. (dec) | 4 |
| NH$_2$OCH$_2$Ph | 1-Azabicyclo[2.2.1]-heptan-3-one, O-(phenylmethyl)oxime hydrochloride, m.p. 173-174° C. | 5 |
| NH$_2$OCH$_2$CH$_2$CH$_3$ | 1-Azabicyclo[2.2.1]-heptan-3-one, O-propyloxime hydrochloride, m.p. 165-166° C. | 6 |
| NH$_2$OCH(CH$_3$)$_2$ | 1-Azabicyclo[2.2.1]-heptan-3-one, O-(1-methylethyl)oxime hydrochloride, m.p. 188-189° C. | 7 |
| NH$_2$OCH$_2$CH=CH$_2$ | 1-Azabicyclo[2.2.1]-heptan-3-one, O-(2-propenyl)oxime oxalate, m.p. 126-127° C. | 8 |
| NH$_2$OCH$_2$CH$_2$NH$_2$ | 1-Azabicyclo[2.2.1]-heptan-3-one, O-(2-aminoethyl)oxime hydrochloride, m.p. 232-234° C. | 9 |
| NH$_2$OCH$_2$-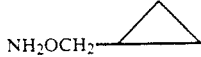 | 1-Azabicyclo[2.2.1]-heptan-3-one, O-(cyclopropylmethyl)-oxime hydrochloride, m.p. 165-167° C. | 10 |
| NH$_2$OCH$_2$CH$_2$OCH$_3$ | 1-Azabicyclo[2.2.1]-heptan-3-one, O-(2-methoxyethyl)oxime hydrochloride, m.p. 176-178° C. | 11 |
| NH$_2$OPh | 1-Azabicyclo[2.2.1]-heptan-3-one, O-phenyloxime hydrochloride, m.p. 130-131° C. | 12 |
| NH$_2$OCH$_2$-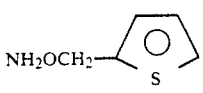 | 1-Azabicyclo[2.2.1]-heptan-3-one, O-(2-thienylmethyl)oxime hydrochloride, m.p. 188-191° C. | 13 |
| NH$_2$OCH$_2$-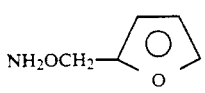 | 1-Azabicyclo[2.2.1]-heptan-3-one, O-(2-furylmethyl)oxime oxalate, m.p. 116-117° C. | 14 |
| NH$_2$OCH$_2$-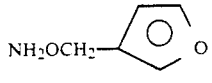 | 1-Azabicyclo[2.2.1]-heptan-3-one, O-(3-furylmethyl)oxime hydrochloride, m.p. 120-122° C. | 15 |
| NH$_2$OCH(CH$_3$)CH=CH$_2$ | 1-Azabicyclo[2.2.1]- | 16 |

TABLE 1-continued

| Hydroxylamine.HCl | Product | Example No. |
|---|---|---|
| | heptan-3-one, O-(1-methyl-2-propenyl)oxime oxalate, m.p. 120–122° C. | |
| $NH_2OCH_2CH_2CH=CH_2$ | 1-Azabicyclo[2.2.1]-heptan-3-one, O-(3-butenyl)oxime oxalate, m.p. 96–98° C. | 17 |
| $NH_2OC(CH_3)_3$ | 1-Azabicyclo[2.2.1]-heptan-3-one, O-(tert-butyl)oxime hydrochloride, m.p. 231–232° C. | 18 |
| $NH_2OCH_2-C\equiv C-CH_3$ | 1-Azabicyclo[2.2.1]-heptan-3-one, O-(2-butynyl)oxime oxalate, m.p. 68–70° C. | 19 |
| $NH_2OCH_2CH_2-C\equiv CH$ | 1-Azabicyclo[2.2.1]-heptan-3-one, O-(3-butynyl)oxime oxalate, m.p. 177–178° C. | 20 |
| $NH_2OCH(CH_3)C\equiv CH$ | 1-Azabicyclo[2.2.1]-heptan-3-one, O-(1-methyl-2-propynyl)oxime oxalate, m.p. 108–111° C. | 21 |
| $NH_2OCH_2CH=CH-C\equiv CH$ | 1-Azabicyclo[2.2.1]-heptan-3-one, O-(E-2-penten-4-ynyl)oxime hydrochloride, m.p. 130–134° C. | 22 |
| $NH_2OCH_2CH=CH-C\equiv CH$ | 1-Azabicyclo[2.2.1]-heptan-3-one, O-(Z-2-penten-4-ynyl)oxime hydrochloride | 23 |
| $NH_2OCH_2C\equiv C-CH=CH_2$ | 1-Azabicyclo[2.2.1]-heptan-3-one, O-(2-pentyn-4-enyl)oxime hydrochloride | 24 |
| $NH_2OCH_2C\equiv C-C\equiv CH$ | 1-Azabicyclo[2.2.1]-heptan-3-one, O-(2,4-pentadiynyl)oxime hydrochloride | 25 |
| $NH_2O-CH(C\equiv CH)_2$ | 1-Azabicyclo[2.2.1]-heptan-3-one, O-(1-ethynylpropynyl)-oxime hydrochloride | 26 |
| $H_2NOCH_2C\equiv N$ | [[(1-Azabicyclo[2.2.1]-hept-3-ylidene)amino]-oxy]acetonitrile hydrochloride, m.p. 202–203° C. | 27 |
| $H_2NOCH_2CH=CH-CH=CH_2$ | 1-Azabicyclo[2.2.1]-heptan-3-one, O-(2,4-pentadienyl)oxime hydrochloride, m.p. 150–154° C. | 28 |
| $H_2NOCH_2CH=CH-CH=CHCH_3$ | 1-Azabicyclo[2.2.1]-heptan-3-one, O-(2,4-hexadienyl)oxime hydrochloride, m.p. 179–180° C. | 29 |
| $H_2NOCH_2CH=CHCH_3$ | 1-Azabicyclo[2.2.1]-heptan-3-one, O-(Z-2-butenyl)oxime oxalate, m.p. 135–140° C. | 30 |
| $H_2NOCH_2CH=CHCH_3$ | 1-Azabicyclo[2.2.1]-heptan-3-one, O-(E-2-butenyl)oxime hydrochloride, m.p. 154–156° C. | 31 |
| $H_2NOCH_2C\equiv CCH_2C\equiv CH$ | 1-Azabicyclo[2.2.1]-heptan-3-one, O-(2,5-hexadiynyl)oxime oxalate, m.p. 144–146° C. | 32 |
| $H_2NOCH_2CH=CH-C\equiv CH$ | 1-Azabicyclo[2.2.1]-heptan-3-one, O-(2-penten-4-ynyl)oxime oxalate, m.p. 130–134° C. | 33 |
| $H_2NOCH_2C\equiv C-CH_2OCH_3$ | 1-Azabicyclo[2.2.1]-heptan-3-one, O-(4-methoxy-2-butynyl)oxime | 34 |

TABLE 1-continued

| Hydroxylamine.HCl | Product | Example No. |
|---|---|---|
| | hydrochloride. m.p. 193–195° C. | |
| $H_2NOCH_2CO_2CH_3$ | [[(1-Azabicyclo[2.2.1] heptan-3-ylidene) amino]oxy] acetic acid methyl ester hydrochloride, m.p. 174–175° C. | 35 |
| $H_2NOCH_2C{\equiv}CCH_2CH_3$ | 1-Azabicyclo[2.2.1] heptan-3-one, O-(2-pentynyl)oxime hydrochloride, m.p. 147–149° C. | 36 |
| $H_2NOCH_2CO_2CH_2CH_3$ | [[(1-Azabicyclo[2.2.1]-heptan-3-ylidene)amino]-oxy]acetic acid ethyl ester hydrochloride, m.p. 198–200° C. | 37 |
| $H_2NOCH_2CO_2CH_2{-}CH{=}CH_2$ | [[(1-Azabicyclo[2.2.1]-heptan-3-ylidene)amino]-oxy]acetic acid 2-propynyl ester hydrochloride, m.p. 179–180° C. | 38 |
| $H_2NOCH_2CH{=}CHCO_2CH_3$ | 4-[[(1-Azabicyclo[2.2.1] hept-3-ylidene)amino]-oxy]-2-butenoic acid methyl ester hydrochloride. m.p. 182–186° C. | 39 |
| $H_2NO(CH_2)_2O(CH_2)_2{-}OCH_3$ | 1-Azabicyclo[2.2.1]-heptan-3-one, O-[2-(2-methoxyethoxy)ethyl]oxime hydrochloride, m.p. 80–82° C. | 40 |
| $H_2NOCH_2CONHCH_3$ | 2-[(1-Azabicyclo[2.2.1]-heptan-3-ylideneamino)-oxy]-N-methyl acetamide oxalate. m.p. 152–156° C. | 41 |
| $H_2NOCH_2CONHCH_2CH_3$ | 2-[(1-Azabicyclo[2.2.1]-heptan-3-ylideneamino)-oxy]-N-ethyl acetamide oxalate. m.p. 194.5–197.5° C. | 42 |
| $H_2NOCH_2CON(CH_3)_2$ | 2-[(1-Azabicyclo[2.2.1]-heptan-3-ylideneamino)-oxy]-N,N-dimethyl acetamide oxalate | 43 |
| $H_2NOCH_2CON(CH_2{-}CH_3)_2$ | 2-[(1-Azabicyclo[2.2.1]-heptan-3-ylideneamino)-oxy]-N,N-diethyl acetamide oxalate. m.p. 109–117° C. | 44 |
| $H_2NOCH_2CONHPh$ | 2-[(1-Azabicyclo[2.2.1]-heptan-3-ylideneamino)-oxy]-N-phenylacetamide | 45 |
| $H_2NOCH_2CONHCH_2Ph$ | 2-[(1-Azabicyclo[2.2.1]-heptan-3-ylideneamino)-oxy]-N-methylphenyl acetamide | 46 |
| $H_2NOCH_2C{\equiv}CCH_2{-}\mathrm{N{\diagup}{\diagdown}O}$ (morpholine) | 1-Azabicyclo[2.2.1]-heptan-3-one, O-[4-(4-morpholinyl)-2-butynyl oxime oxalate, m.p. 145.5–148.5° C. | 47 |

EXAMPLE 48

1-Azabicyclo2.2.2]octan 3-one, O-methyloxime

A mixture of the ketoamine·HCl (5.56 g, 0.03 mole), 3-quinuclidinone (2.51 g, 0.03 mole), and potassium carbonate (11.0 g, 0.08 mole) in methanol (250 mL) was allowed to reflux for 2 hours. After removing the methanol under reduced pressure, the solution was suspended in water and extracted with ethyl ether (3 × 125 mL), dried over $MgSO_4$, filtered, and concentrated to give a mixture of Z and E isomers. The oxalate salt was formed from the oil, m.p. 125°–28° C.

$^1$H NMR (CDCl$_3$) 9.01 (br s, 2H), 4.03 (s, 1H), 3.89 (s, 1H), 3.80, 3.79 (two s, 3H). 3.27–3.12 (br m, 5H), 2.10–1.79 (br m, 4H). $^{13}$C NMR: δ 164.7, 155.1, 154.6, 61.4, 59.4, 50.7, 50.1, 45.6, 45.5, 26.7, 22.5, 22.1, 21.4, 21.2 IR (cm$^{-1}$) 2361, 1748, 1693, 1652, 1463, 1403, 1320, 1221, 1103, 1048, 861, 832, 785, 721, 670.

Mass Spec.: 154, 137, 123, 108, 97, 82, 67, 55.

C, H, N $C_8H_{14}N_2O\cdot 1.25C_2H_2O_4$: Calc.: C, 47.28; H, 6.23; N, 10.50. Found: C, 47.57; H, 6.32; N, 10.27.

EXAMPLE 49

(E)- and (Z)- 1-Azabicyclo[2.2.2]octan-3-one, O-(2-propynyl)oxime

3-Quinuclidinone (1.5 g, 12 mmol) and 2-propynyl-hydroxylamine hydrochloride (1.29 g, 12 mmol) were dissolved in 20 mL of methanol and stirred at room temperature for 16 hours. The reaction was evaporated in vacuo to afford a dark brown semi-slid. The crude semi-solid was basified with aqueous $K_2CO_3$ and extracted with chloroform. The chloroform extract was evaporated to give the crude oxime as a mixture of the E- and Z-isomers. Separation of the isomers by chromatography (silica gel; dichloromethane-acetone-methanol (150:10:5), gave isomer A, 1.0 g (m.p. 81°-83° C.) and isomer B, 0.42 g (m.p. 100°-101° C.), respectively.

Isomer A:

$C_{10}H_{14}N_2O$: Calc.: C, 67.39; H, 7.92; N, 15.72. Found: C, 67.26; H, 7.94; N, 15.59.

Mass Spec.: m/e 178

$^1H$ NMR: $\delta$ (CDCl$_3$) 1.7–1.85 (4H, m); 2.40–2.55 (1H, m), 2.58–2.65 (1H, m), 2.75–3 05 (4H, m), 3.63 (2H, s), 4.62 (2H, s). $^{13}C$ NMR: $\delta$ (CDCl$_3$) 26.3, 28.6, 47.2, 52.3, 60.9, 74.2, 81.0, 166.0.

Isomer B:

$C_{10}H_{14}N_2O$; Calc.: C, 67.39; H, 7.92; N, 15.72. Found: C, 66.95; H, 8.02; N, 15.59.

Mass Spec.: m/e 178

$^1H$ NMR: $\delta$ (CDCl$_3$) 1.6–1.8 (4H, m), 2.45–2.50 (1H, m), 2.78–3.0 (4H, m), 3.35–3.44 (1H, m), 3.45 (2H, s), 4.6 (2H, s). $^{13}C$ NMR: $\delta$ (CDCl$_3$) 23.5, 24.8, 47.2, 53.6, 60.8, 70.1, 81.0, 165.0.

EXAMPLE 50

4-Piperidinone O-methyloxime hydrochloride

4-Piperidinone hydrochloride monohydrate (5 g, 32.5 mmol), methoxyamine hydrochloride (4.18 g, 50 mmol) and potassium carbonate (13.82 g, 100 mmol) were taken into 100 mL of ethanol and stirred at room temperature for 16 hours. The reaction mixture was filtered and the filtrate evaporated to afford a white solid. The crude solid was dissolved in water, made basic with solid potassium carbonate, and extracted with dichloromethane (3×100 mL). The combined extracts were dried over anhydrous sodium sulfate and evaporated in vacuo to afford a clear, colorless liquid. It was converted to its hydrochloride salt by treating with ethereal hydrogen chloride to give 233 g, m.p. 140°-141° C. $C_6H_{12}N_2O \cdot HCl$: Calc.: C, 43.77; H, 7.96; N, 17.02. Found: C, 43.78; H, 7.96; N, 17.08.

$^1H$ NMR: $\delta$ (CDCl$_3$) 2.68–2.73 (t, 2H), 2.92–2.97 (t, 2H), 3.27–3.34 (m, 4H), 3.84 (s, 3H), 9.93 (br.s, 1H). $^{13}$NMR: $\delta$ (CDCl$_3$) 21.76, 28.05, 42.92, 44.29, 61.61, 150.07.

Mass Spec.: m/e 128.08 (M+ for free base).

EXAMPLE 51

1-Methyl-4-piperidinone O-methyloxime hydrochloride

1-Methyl-4 piperidone (5 g, 44.2 mmol) and methoxyamine hydrochloride (3.69 g, 44.2 mmol) were taken into 25 mL of methanol and stirred at room temperature for 2 days. The reaction mixture was evaporated in vacuo to afford a solid residue. The residue was dissolved in water, made basic with solid potassium carbonate, and extracted with dichloromethane (3×100 mL). The combined extracts were dried over anhydrous sodium sulfate and evaporated to give a clear, yellow liquid that was purified on silica gel, eluting with dichloromethane-methanol (95:5) to afford 2.55 g of the desired product. Treatment with ethereal hydrogen chloride gave the hydrochloride salt, 2.99 g, m.p. 145°-147° C.

$C_7H_{14}N_2O \cdot HCl$: Calc.: C, 47.06; H, 8.46; N, 15.68. Found: C, 46.94; H, 8.41; N, 15.60.

$^1H$ NMR: $\delta$ (CDCl$_3$) 2.53–2.58 (m, 1H), 2.69–3.20 (m, 4H), 2.87–2.89 (d, 3H), 3.36–3.49 (m, 1H), 3.55–3.76 (m, 2H), 3.84 (s, 3H), 12.90 (br.s, 1H). $^{13}C$ NMR: $\delta$ (CDCl$_3$) 21.97, 28.25, 43.46, 53.09, 54.36, 61.64, 149.17.

Mass spec.: m/e 142.17 (M+) for free base).

EXAMPLE 52

Z-($\pm$)-1-Azabicyclo2.2.1]heptan-3-one
O-2-propenyloxime oxalate and
E-($\pm$)-1-azabicyclo[2.2.1]-heptan-3-one
O-2-propenyloxime oxalate 1-Azabicyclo[2.2.1]heptan-3-one (2 g, 18 mmol) and O-allylhydroxylamine hydrochloride hydrate (1.97 g, 18 mmol) were dissolved in 25 mL of methanol and stirred at room temperature for 18 hours. The reaction was evaporated in vacuo to give a viscous oil. The crude oil was dissolved in 50 mL of water, made basic with a saturated solution of potassium carbonate, and extracted with ether (3×100 mL). The combined extracts were dried over anhydrous sodium sulfate, and evaporated to give a clear, yellow liquid which was purified on silica gel, eluting with dichloromethane methanol (10:1). Isomer A, the less polar isomer, was isolated and converted to the oxalate salt to give 1.365 g, m.p. 130°–132° C. $C_9H_{14}N_2O \cdot C_2H_2O_4$: Calc.: C, 5.55; H, 6.29; N, 10.93. Found: C, 51.52; H, 6.37; N, 10.88.

$^1H$ NMR: $\delta$ (DMSO) 12.0 (br.s, 2H), 5.86–6.02 (m, 1H), 5.17–5.31 (m, 2H), 4.5–4.52 (d, 2H), 3.85–4.06 (q, 2H), 3.16–3.42 (m, 5H), 2.14–2.27 (m, 1H), 1.70–1.75 (m, 1H).

Mass Spec.: m/e 166.1 (M+ for free base)

Isomer B, the more polar isomer, was converted to the oxalate to give 0.829 g, m.p. 102°–104° C.

$C_9H_{14}N_2O \cdot C_2H_2O_4$ Calc.: C, 51.55; H, 6.29; N, 10.93. Found: C, 51.02; H, 6.22; N, 10.63.

$^1H$ NMR: $\delta$ (DMSO) 11.2 (br.s, 2H), 5.88–6.04 (m, 1H), 5.17–5.33 (m, 2H), 4.50–4.55 (d, 2H), 3.73–4.00 (m, 3H), 3.11–3.42 (m, 4H), 2.08–2.21 (m, 1H), 1.62–1.66 (m, 1H).

Mass Spec.: m/e 166.1 (M+ for free base).

The above procedure was utilized for the synthesis of the following E and Z isomers:

TABLE 2

| Example No. | Amine | Product |
| --- | --- | --- |
| 53 | H$_2$NOCH$_2$C≡CH.HCl | Z-($\pm$)-1-azabicyclo-[2.2.1]heptan-3-one, O-2-propynyloxime hydrochloride, m.p. 199–200° C. |

TABLE 2-continued

| Example No. | Amine | Product |
|---|---|---|
| 54 | H₂NOCH₂–(3-thienyl).HCl | Z-(±)-1-azabicyclo-[2.2.1]heptan-3-one, O-(3-thienylmethyl)oxime oxalate, m.p. 142–144° C. |
| 55 | H₂NOCH₂–(3-thienyl).HCl | E-(±)-1-azabicyclo-[2.2.1]heptan-3-one, O-(3-thienylmethyl)oxime oxalate, m.p. 142–143° C. |
| 56 | H₂NO-CH₂-C(=CH₂)-.HCl | Z-(±)-1-azabicyclo-[2.2.1]heptan-3-one, O-(2-methyl-2-propenyl)-oxime oxalate; m.p. 131–133° C. |
| 57 | H₂NO-CH₂-C(=CH₂)-.HCl | E-(±)-1-azabicyclo-[2.2.1]heptan-3-one, O-(2-methyl-2-propenyl)-oxime oxalate, m.p. 124–126° C. |
| 58 | H₂NO-cyclobutyl.HCl | Z-(±)-1-azabicyclo-[2.2.1]heptan-3-one, O-cyclobutyloxime hydrochloride, m.p. 209–210° C. |
| 59 | H₂NO-cyclobutyl.HCl | E-(±)-1-azabicyclo-[2.2.1]heptan-3-one, O-cyclobutyloxime hydrochloride, m.p. 207–208° C. |
| 60 | H₂NO(CH₂)₃C≡CH.HCl | Z-(±)-1-azabicyclo-[2.2.1]heptan-3-one, O-4-pentynyloxime oxalate, m.p. 119–121° C. |
| 61 | H₂NO(CH₂)₃C≡CH.HCl | E-(±)-1-azabicyclo-[2.2.1]heptan-3-one, O-4-pentynyloxime oxalate, m.p. 110–113° C. |
| 62 | H₂NO(CH₂)₂C≡CCH₃.HCl | Z-(±)-1-azabicyclo-[2.2.1]heptan-3-one, O-3-pentynyloxime oxalate, m.p. 161–162° C. |
| 63 | H₂NO(CH₂)₂C≡C—CH₃.HCl | E-(±)-1-azabicyclo-[2.2.1]heptan-3-one, O-3-pentynyloxime oxalate, m.p. 149–150° C. |
| 64 | H₂NOCH₂C≡CCH₂C≡CCH₃.HCl | Z-(±)-1-azabicyclo [2.2.1]heptan-3-one, O-(2,5-heptadiynyl)oxime oxalate, m.p. 65–70° C. |
| 65 | H₂NOCH₂C≡CCH₂C≡CCH₃.HCl | E-(±)-1-azabicyclo [2.2.1]heptan-3-one, O-(2,5-heptadiynyl)oxime oxalate, m.p. 108–110° C. |
| 66 | H₂NOCH₂C≡CCH₂CH=CH₂.HCl | Z-(±)-1-azabicyclo [2.2.1]heptan-3-one, O-(2-hexyn-5-enyl)oxime oxalate, m.p. 94–96° C. |
| 67 | H₂NOCH₂C≡C—Ph.HCl | Z-(±)-1-azabicyclo [2.2.1]heptan-3-one, O-(3-phenyl-2-propynyl) oxime oxalate, m.p. 162–164° C. |
| 68 | H₂NOCH₂C≡C—Ph.HCl | E-(±)-1-azabicyclo [2.2.1]heptan-3-one, O-(3-phenyl-2-propynyl) oxime oxalate, m.p. 83–85° C. |
| 69 | H₂NOCH₂C≡C—C(CH₃)=CH₂.HCl | Z-(±)-1-azabicyclo [2.2.1]heptan-3-one, O-(4-methyl-2-pentyn-4-enyl)oxime oxalate, m.p. 118–119° C. |
| 70 | H₂NOCH₂C≡CC(CH₃)=CH₂.HCl | E-(±)-1-azabicyclo [2.2.1]heptan-3-one, O-(4-methyl-2-pentyn-4-enyl)oxime oxalate, m.p. 78–83° C. |
| 71 | H₂NOCH₂C≡C(CH₂)₂CH₃.HCl | Z-(±)-1-azabicyclo [2.2.1]heptan-3-one, O-(2-hexynyl)oxime oxalate, m.p. 109–110° C. |
| 72 | H₂NOCH₂C≡C(CH₂)₂CH₃.HCl | E-(±)-1-azabicyclo [2.2.1]heptan-3-one, O-(2-hexynyl)oxime oxalate, m.p. 105–107° C. |
| 73 | H₂NOCH₂C≡C(CH₂)₃CH₃.HCl | Z-(±)-1-azabicyclo [2.2.1]heptan-3-one, O-(2-heptynyl)oxime oxalate, m.p. 109–110° C. |
| 74 | H₂NOCH₂C≡C(CH₂)₃CH₃.HCl | E-(±)-1-azabicyclo [2.2.1]heptan-3-one, O-(2-heptynyl)oxime oxalate, m.p. 100–104° C. |
| 75 | H₂NOCH₂CH₂SCH₂C≡CH.HCl | Z-(±)-1-azabicyclo [2.2.1]heptan-3-one, O-(2-(2-propynylthio) ethyl)oxime |

TABLE 2-continued

| Example No. | Amine | Product |
|---|---|---|
| 76 | H$_2$NOCH$_2$CH$_2$SCH$_2$C≡CH.HCl | E-(±)-1-azabicyclo [2.2.1]heptan-3-one, O-(2-(2-propynylthio) ethyl)oxime oxalate, m.p. 121–122° C. |
| 77 | H$_2$NOCH$_2$C≡CCH$_2$C≡CCH$_2$C≡CH.HCl | Z-(±)-1-Azabicyclo[2.2.1]heptan-3-one, O-(2,5,8-nonatriynyl)oxime oxalate, mp. 113–117° C. |
| 78 | H$_2$NOCH$_2$C≡CCH$_2$C≡CCH$_2$C≡CH.HCl | E-(±)-1-Azabicyclo[2.2.1]heptan-3-one, O-(2,5,8-nonatriynyl)oxime oxalate, m.p. 129–132° C. |
| 79 | H$_2$NOCH$_2$—C=C—C≡CH.HCl (H, CH$_3$) | Z-(±)-1-Azabicyclo[2.2.1]heptan-3-one, O-(Z-3-methyl-2-penten-4-ynyl)oxime oxalate, m.p. 127–129° C. |
| 80 | H$_2$NOCH$_2$—C=C—C≡CH.HCl (H, CH$_3$) | E-(±)-1-Azabicyclo[2.2.1]heptan-3-one, O-(Z-3-methyl-2-penten-4-ynyl)oxime oxalate, m.p. 125–128° C. |
| 81 | H$_2$NOCH$_2$—C=C—C≡CH.HCl (H / CH$_3$) | Z-(±)-1-Azabicyclo[2.2.1]heptan-3-one, O-(E-3-methyl-2-penten-4-ynyl)oxime oxalate, m.p. 125–128° C. |
| 82 | H$_2$NOCH$_2$—C=C—C≡CH.HCl (H / CH$_3$) | E-(±)-1-Azabicyclo[2.2.1]heptan-3-one, O-(E-3-methyl-2-penten-4-ynyl)oxime oxalate, m.p. 140–142° C. |
| 83 | H$_2$NOCH$_2$C≡CCH(CH$_3$)$_2$.HCl | Z-(±)-1-Azabicyclo[2.2.1]heptan-3-one, O-(4-methyl-2-pentynyl)oxime oxalate, m.p. 133–134° C. |
| 84 | H$_2$NOCH$_2$C≡CCH(CH$_3$)$_2$.HCl | E-(±)-1-Azabicyclo[2.2.1]heptan-3-one, O-(4-methyl-2-pentynyl)oxime oxalate, m.p. 111–112° C. |
| 85 | H$_2$NOCH$_2$C≡CC(CH$_3$)$_3$.HCl | Z-(±)-1-Azabicyclo[2.2.1]heptan-3-one, O-(4,4-dimethyl-2-pentynyl)oxime oxalate, m.p. 157–158° C. |
| 86 | H$_2$NOCH$_2$C≡CC(CH$_3$)$_3$.HCl | E-(±)-1-Azabicyclo[2.2.1]heptan-3-one, O-(4,4-dimethyl-2-pentynyl)oxime oxalate, m.p. 150–152° C. |
| 87 | H$_2$NOCH$_2$C≡C—C$_6$H$_4$—OCH$_3$.HCl | Z-(±)-1-Azabicyclo[2.2.1]heptan-3-one, O-(3-(4'-methoxyphenyl)-2-propynyl)-oxime oxalate, m.p. 158–159° C. |
| 88 | H$_2$NOCH$_2$C≡C—C$_6$H$_4$—OCH$_3$.HCl | E-(±)-1-Azabicyclo[2.2.1]heptan-3-one, O-(3-(4'-methoxyphenyl)-2-propynyl)-oxime oxalate, m.p. 147–148° C. |
| 89 | H$_2$NOCH$_2$C≡C—C$_6$H$_4$(OCH$_3$).HCl | Z-(±)-1-Azabicyclo[2.2.1]heptan-3-one, O-(3-(3'-methoxyphenyl)-2-propynyl)-oxime oxalate, m.p. 126–127° C. |
| 90 | H$_2$NOCH$_2$C≡C—C$_6$H$_4$(OCH$_3$).HCl | E-(±)-1-Azabicyclo[2.2.1]heptan-3-one, O-(3-(3'-methoxyphenyl)-2-propynyl)-oxime oxalate, m.p. 80–82° C. |
| 91 | H$_2$NOCH$_2$C≡C—C$_6$H$_4$(OCH$_3$).HCl | Z-(±)-1-Azabicyclo[2.2.1]heptan-3-one, O-(3-(2'-methoxyphenyl)-2-propynyl) oxime oxalate, m.p. 155–157° C. |

TABLE 2-continued

| Example No. | Amine | Product |
|---|---|---|
| 92 | 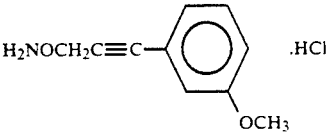 | E-(±)-1-Azabicyclo[2.2.1]heptan-3-one, O-(3-(2'-methoxyphenyl)-2-propynyl)-oxime oxalate, m.p. 132–133° C. |
| 93 | 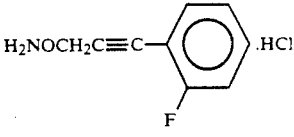 | Z-(±)-1-Azabicyclo[2.2.1]heptan-3-one, O-(3-(2'-fluorophenyl)-2-propynyl)oxime oxalate, m.p. 141–142° C. |
| 94 | 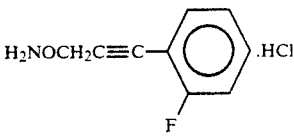 | E-(±)-1-Azabicyclo[2.2.1]heptan-3-one, O-(3-(2'-fluorophenyl)-2-propynyl)oxime oxalate, m.p. 83–85° C. |
| 95 | 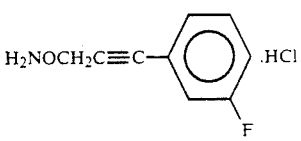 | Z-(±)-1-Azabicyclo[2.2.1]heptan-3-one, O-(3-(3'-fluorophenyl)-2-propynyl)oxime oxalate, m.p. 123–125° C. |
| 96 | 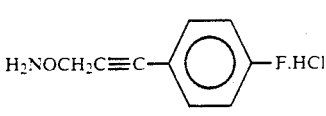 | Z-(±)-1-Azabicyclo[2.2.1]heptan-3-one, O-(3-(4'-fluorophenyl)-2-propynyl)oxime oxalate, m.p. 144–145° C. |
| 97 | 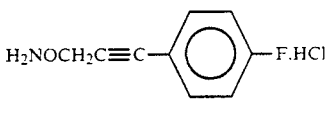 | E-(±)-1-Azabicyclo[2.2.1]heptan-3-one, O-(3-(4'-fluorophenyl)-2-propynyl)oxime oxalate, m.p. 140–143° C. |
| 98 | 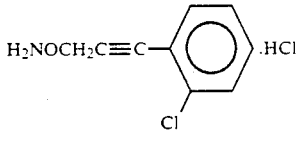 | Z-(±)-1-Azabicyclo[2.2.1]heptan-3-one, O-(3-(2'-chlorophenyl)-2-propynyl)oxime oxalate, m.p. 143–145° C. |
| 99 | 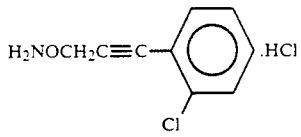 | E-(±)-1-Azabicyclo[2.2.1]heptan-3-one, O-(3-(2'-chlorophenyl)-2-propynyl)oxime oxalate, m.p. 102–104° C. |
| 100 | 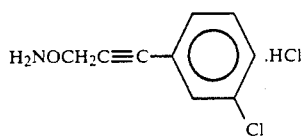 | Z-(±)-1-Azabicyclo[2.2.1]heptan-3-one, O-(3-(3'-chlorophenyl)-2-propynyl)oxime oxalate, m.p. 140–142° C. |
| 101 | 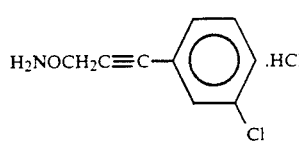 | E-(±)-1-Azabicyclo[2.2.1]heptan-3-one, O-(3-(3'-chlorophenyl)-2-propynyl)oxime oxalate, m.p. 114–116° C. |
| 102 | 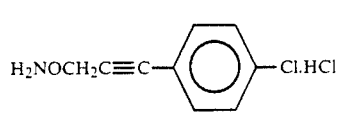 | Z-(±)-1-Azabicyclo[2.2.1]heptan-3-one, O-(3-(4'-chlorophenyl)-2-propynyl)oxime oxalate, m.p. 163–164° C. |

TABLE 2-continued

| Example No. | Amine | Product |
|---|---|---|
| 103 | H₂NOCH₂C≡C—⟨phenyl⟩—CH₃·HCl | Z-(±)-1-Azabicyclo[2.2.1]heptan-3-one, O-(3-(4'-methylphenyl)-2-propynyl)oxime oxalate, m.p. 157-158° C. |
| 104 | H₂NOCH₂C≡C—⟨phenyl-NO₂⟩·HCl | Z-(±)-1-Azabicyclo[2.2.1]heptan-3-one, O-(3-(3'-nitrophenyl)-2-propynyl)oxime oxalate, m.p. 157-160° C. |
| 105 | H₂NOCH₂C≡C—⟨phenyl-NO₂⟩·HCl | E-(±)-1-Azabicyclo[2.2.1]heptan-3-one, O-(3-(3'-nitrophenyl)-2-propynyl)oxime oxalate, m.p. 131-132° C. |
| 106 | H₂NOCH₂C≡C—⟨2-thienyl⟩·HCl | Z-(±)-1-Azabicyclo[2.2.1]heptan-3-one, O-(3-(2-thienyl)-2-propynyl)oxime oxalate, m.p. 135-136° C. |
| 107 | H₂NOCH₂C≡C—⟨2-thienyl⟩·HCl | E-(±)-1-Azabicyclo[2.2.1]heptan-3-one, O-(3-(2-thienyl)-2-propynyl)oxime oxalate, m.p. 96-98° C. |
| 108 | H₂NOCH₂C≡C—⟨3-thienyl⟩·HCl | Z-(±)-1-Azabicyclo[2.2.1]heptan-3-one, O-(3-(3-thienyl)-2-propynyl)oxime oxalate, m.p. 146-148° C. |
| 109 | H₂NOCH₂C≡C—⟨3-thienyl⟩·HCl | E-(±)-1-Azabicyclo[2.2.1]heptan-3-one, O-(3-(3-thienyl)-2-propynyl)oxime oxalate, m.p. 90-92° C. |
| 110 | H₂NOCH₂C≡C—⟨pyridinyl⟩·HCl | Z-(±)-1-Azabicyclo[2.2.1]heptan-3-one, O-(3-(3-pyridinyl)-2-propynyl)oxime dioxalate, m.p. 160-162° C. |
| 111 | H₂NOCH₂CH₂—⟨phenyl⟩·C₂H₂O₄ | Z-(±)-1-Azabicyclo[2.2.1]heptan-3-one, O-(2-phenylethyl)oxime oxalate, m.p. 143-145° C. |
| 112 | H₂NOCH₂CH₂—⟨phenyl⟩·C₂H₂O₄ | E-(±)-1-Azabicyclo[2.2.1]heptan-3-one, O-(2-phenylethyl)oxime oxalate, m.p. 140-142° C. |
| 113 | H₂NOCH₂CH₂O—⟨phenyl⟩·HCl | Z-(±)-1-Azabicyclo[2.2.1]heptan-3-one, O-(2-phenoxyethyl)oxime oxalate, m.p. 140-142° C. |
| 114 | H₂NOCH₂CH₂O—⟨phenyl⟩·HCl | E-(±)-1-Azabicyclo[2.2.1]heptan-3-one, O-(2-phenoxyethyl)oxime oxalate, m.p. 122-125° C. |
| 115 | H₂NOCH₂CH₂CH₂—⟨phenyl⟩·C₂H₂O₄ | Z-(±)-1-Azabicyclo[2.2.1]heptan-3-one, O-(3-phenylpropyl)oxime oxalate, m.p. 108-110° C. |

TABLE 2-continued

| Example No. | Amine | Product |
|---|---|---|
| 116 | H₂NOCH₂CH₂CH₂—⟨phenyl⟩·C₂H₂O₄ 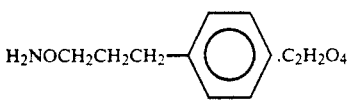 | E-(±)-1-Azabicyclo[2.2.1]heptan-3-one, O-(3-phenylpropyl)oxime oxalate, m.p. 130–131° C. |
| 117 | N₂NOCH₂CH=C(CH₃)₂.HCl | Z-(±)-1-Azabicyclo[2.2.1]heptan-3-one, O-(3-methyl-2-butenyl)oxime oxalate, m.p. 130–131° C. |
| 118 | N₂NOCH₂CH=C(CH₃)₂.HCl | E-(±)-1-Azabicyclo[2.2.1]heptan-3-one, O-(3-methyl-2-butenyl)oxime oxalate, m.p. 131–132° C. |
| 119 | H₂NOCH₂CH=C(CH₃)CH₂CH₂CH=C(CH₃)₂.HCl | Z-(±)-1-Azabicyclo[2.2.1]heptan-3-one, O-(3,7-dimethyl-2,6-octadienyl)oxime oxalate, m.p. 103–104° C. |
| 120 | H₂NOCH₂C(H)=C(CH₃)—C≡C—⟨phenyl⟩·HCl 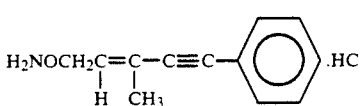 | Z-(±)-1-Azabicyclo[2.2.1]heptan-3-one, O-(Z-3-methyl-5-phenyl-2-penten-4-ynyl)oxime oxalate, m.p. 137–141° C. |
| 121 | H₂NOCH₂C(H)=C(CH₃)—C≡C—⟨phenyl⟩·HCl 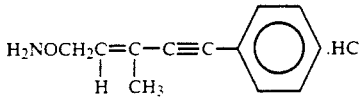 | E-(±)-1-Azabicyclo[2.2.1]heptan-3-one, O-(Z-3-methyl-5-phenyl-2-penten-4-ynyl)oxime oxalate, m.p. 106–110° C. |
| 122 | H₂NOCH₂C(H)=C(CH₃)—C≡C—⟨phenyl⟩·HCl 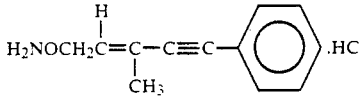 | Z-(±)-1-Azabicyclo[2.2.1]heptan-3-one, O-(E-3-methyl-5-phenyl-2-penten-4-ynyl)oxime oxalate, m.p. 133–134° C. |
| 123 | H₂NOCH₂C(H)=C(CH₃)—C≡C—⟨phenyl⟩·HCl 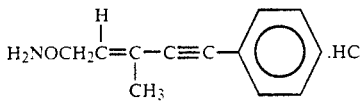 | E-(±)-1-Azabicyclo[2.2.1]heptan-3-one, O-(E-3-methyl-5-phenyl-2-penten-4-ynyl)oxime oxalate, m.p. 129–131° C. |

EXAMPLE 124

N-Methyl-8-Azabicyclo octan-3-one methyl oxime hydrochloride

A solution of methoxyamine hydrochloride (4.18 g, 0.05 mol) in methanol was added to a rapidly stirring solution of N-methyl-8-azabicyclo octan-3-one (commercially available) (6.96 g, 0.05 mol) in methanol while cooling with an ice-bath. The reaction mixture was allowed to warm up to room temperature, stirred at room temperature for 16 hours and then the solvent removed. The resulting solid residue was partitioned between $CH_2Cl_2$ and conc. aqueous $K_2CO_3$ solution. The organic layer was dried ($K_2CO_3$), and concentrated to give an oil. The oil was dissolved in ether and treated with ethereal-HCl. The resulting white solid ppt was separated by filtration and recrystallized from isopropanol-isopropyl ether to give 4.88 g (45%) of oxime hydrochloride as white solid: mp turns brown at 197° C. to 200° C. and melts with decomposition at 217° C. and 220° C; $^1$H NMR ($D_2O$) δ 4.710 (s, 4H), 4.013–3.939 (bd 1H), 3.765 (s, 3H), 3.259–3.194 (bd, 1H), 2.745 (s, 3H), 2.476–2.232 (m, 3H), 1.909–1.722 (m, 1H); $^{13}$C NMR ($D_2O$) δ 154.411, 66.306, 65.520, 64.257, 41.756, 38.930, 33.925, 27.461, 26.657; Mass. Spec. 168 CM⁺ for free base.

EXAMPLE 125

N-Methyl-8 Azabicyclo3.2.1]octan 2 one-O-methyl oxime hydrochloride

The preparation of this compound is depicted in the Flow Chart set forth hereinafter and as described hereinbelow.

(a) Preparation of Ethyl 1,3,4,5-cyclohepta-triene-1-carboxylate (2)

Ethyl diazoacetate (43.4 g, 0.38 mol) was added slowly (syringe pump) over a period of 7 hours to a mixture of benzene (594.32 g, 7.61 mol) and tetrakis(perfluorobenzoato) dirhodium(II) (0.84 g, 00.16 mol). After stirring at room temperature for 16 hours, the solvent was removed and the oily residue distilled in vacuo to give 50.44 g (81%) of ethyl 1,3,5-cycloheptatriene-1-carboxylate: bp 90°–96° C. 2 4–3.0 mm Hg); $^1$H NMR (CDCl₃) δ6.6 (m, 2H), 6.2 (m, 2H), 5.3 (m, 2H), 4.2 (q, 2H OCH₂CH₃), 2.5 (t, 1H), 1.3 (t, 3H CH₂CH₃)

(b) Preparation of N-Methyl Ethyl 8-Azabicyclo-[3.2.1]oct-2-ene-2-carboxylate (3)

A mixture of ethyl 1,3,5-cycloheptatriene 1-carboxylate (12.72 g, 0.077 mol), methylamine (23.13 g, 0.74 mol) and NaOH (3.1 g, 0.078 mol) in MeOH (60 mL) was autoclaved at 125° C. for 26 hours. The reaction mixture was filtered, and the filtrate concentrated to give an oil. The oil was dissolved in MeOH (400 mL) and saturated with HCl gas; conc. sulphuric acid (8 mL)

was added and the mixture refluxed for 12 hours. The oily residue obtained after evaporation of MeOH was partitioned between aqueous conc. $Na_2CO_3$ and $ET_2O$. The ether layer was evaporated as brown oil: Ir (neat) 1720 ($COOCH_3$); $^1H$ NMR ($CDCl_3$) δ 6.8 (bt, 1H), 3.7 (s, 3H $OCH_3$), 2.35 (s, 3H $NCH_3$), 3.4–2.4 (m, 3H), 2.3–1.4 (m, 6H).

(c) Preparation of
N-Methyl-2-acetyl-8-azabicyclo-[3.2.1]oct-2-ene (4)

To a mixture of ethyl trop 2-ene-2-carboxylate (3.43 g, 0.019 mol) and $Me_3SiCl$ (10.32 g, 0.095 mol) in THF (70 mL) cooled to −100° C., MeLi (1.4M, 17.07 mL, 0.0239 mol) was added dropwise. After warming up to room temperature, the reaction mixture was stirred for 16 hours. Excess $Me_3SiCl$ and THF was evaporated off and the resulting residue was stirred with EtOH (6 mL) followed by water (6 mL). The mixture was then made acidic (6N HCl) and extracted with ether. The aqueous layer was made basic (solid $K_2CO_3$) and extracted with chloroform, dried ($K_2CO_3$) and concentrated to give 3.14 g (81%) of 2-acetyltrop-2-ene as an oil: IR (neat) 1670 ($COCH_3$); $^1H$ NMR ($CDCl_3$) δ6.7 (bt, 1H), 2.3 (s, $NCH_3$), 2.2 (s, C(≡O)$CH_3$).

(d) N-Methyl-2-Acetyl 8-azabicyclo[3.2.1]octane, compound (5) is obtained by catalytic reduction ($H_2$/RaNi) of compound (4) and is converted to N-Methyl-8-azabicyclo octan-2 one, compound (7) by procedures known in the art, see *J. Org. Chem.* 55, 5025 (1990). In compound (6) TBDMSO stands for testing butyl dimethylsilyloxy. The ketone, compound (7) is converted to the methyloxime as generally described above in Example 124.

Similarly when N-methyl-2-acetyl-9-azabicyclo 4.2.1]nonane, which can be prepared from 2-acetyl-9-azabicyclo non-2-ene which is commercially available, is substituted for N-methyl-2-acetyl-8-azabicyclo octane, compound (5), N-methyl-8-azabicyclo nonan-2-one methyl oxime is obtained.

Following the general procedure of Example 52 only substituting the hydroxylamine listed below for O-allyl-hydroxylamine hydrochloride hydrate, the products listed below can be prepared.

TABLE 3

| Example No. | Amine.HCl | Product |
|---|---|---|
| 126 | $H_2NOCH_2$—(biphenyl) | Z-(±)-1-Azabicyclo-[2.2.1]heptan-3-one, O-p-biphenyl-yloxime |
| 127 | $H_2NOCH_2$—(cyclohexenyl) | Z-(±)-1-Azabicyclo-[2.2.1]heptan-3-one, O-(cyclohex-2-enylmethyl)oxime, m.p. 127–130° C. |
| 128 | $H_2NOCH_2$—(cyclohexenyl) | E-(±)-1-Azabicyclo-[2.2.1]heptan-3-one, O-(cyclohex-2-enylmethyl)oxime, m.p. 98–100° C. |
| 129 | $H_2NOCH_2C≡CCH_2$—(cyclohexyl) | Z-(±)-1-Azabicyclo-[2.2.1]heptan-3-one, O-[(3-cyclohexylmethyl)-2-propynyl]oxime, m.p. 115–116° C. |
| 130 | $H_2NOCH_2C≡CCH_2$—(cyclohexyl) | E-(±)-1-Azabicyclo-[2.2.1]heptan-3-one, O-[(3-cyclohexylmethyl)-2-propynyl]oxime, m.p. 88–90° C. |
| 131 | $H_2NOCH_2C≡CCH_2$—(cyclopentyl) | Z-(±)-1-Azabicyclo-[2.2.1]heptan-3-one, O-(3-cyclohexylmethyl)-2-propynyl]oxime, m.p. 108–110° C. |
| 132 | $H_2NOCH_2C≡CCH_2$—(cyclopentyl) | E-(±)-1-Azabicyclo-[2.2.1]heptan-3-one, O-[(3-cyclohexylmethyl)-2-propynyl]oxime, m.p. 117–120° C. |
| 133 | $H_2NOCH_2C≡C$—(cyclopentyl) | Z-(±)-1-Azabicyclo-[2.2.1]heptan-3-one, O-[(3-cyclopentyl)-2-propynyl]oxime, m.p. 125–128° C. |
| 134 | $H_2NOCH_2C≡C$—(cyclopentyl) | E-(±)-1-Azabicyclo-[2.2.1]heptan-3-one, O-[(3-cyclopentyl)-2-propynyl]oxime, m.p. 135–136° C. |
| 135 | $H_2NO$—(cyclohexenyl) | 1-Azabicyclo-[2.2.1]heptan-3-one, O-cyclohex-2-enyloxime |
| 136 | $H_2NO$—(cyclopentenyl) | 1-Azabicyclo-[2.2.1]heptan-3-one, O-cyclopent-2-enyloxime |
| 137 | $H_2NOCH_2CH$=(cyclohexenyl) | 1-Azabicyclo-[2.2.1]heptan-3-one, O-2-(cyclohex-2-enylidene)ethyloxime |
| 138 | $H_2NOCH_2CH$=(cyclopentenyl) | 1-Azabicyclo-[2.2.1]heptan-3-one, O-2-(cyclopent-2-enylidene)ethyloxime |
| 139 | $H_2NOCH_2CH$=(cyclohexyl) | 1-Azabicyclo-[2.2.1]heptan-3-one, O-2-(cyclohexylidene)ethyloxime |
| 140 | $H_2NOCH_2CH$=(cyclopentyl) | 1-Azabicyclo-[2.2.1]heptan-3-one, O-2-(cyclopentylidene)ethyloxime |

PREPARATION OF HYDROXYLAMINES

I.
O-(Trans-3-methyl-5-phenyl-2-penten-4-ynyl)-hydroxylamine hydrochloride (a) Trans-3-methyl-5-phenyl-2-penten-4-yn-1-ol Trans-3-methyl-2-penten-4-yn-1-ol (10.57 g, 0.11 mol), diethylamine (80 mL), copper(I)iodide (0.7 g), tetrahydrofuran (30 mL), and tetrakis(triphenylphosphine)palladium(o) (1.0 g) were placed in a 300-mL flask under nitrogen. Iodobenzene (11.2 mL, 0.1 mol) was added dropwise via a dropping funnel at room temperature. After stirring at room temperature for 24 hours, the reaction was evaporated in vacuo to give a brown semisolid residue. The crude residue was dissolved in 200 mL of water, then extracted four times with 200 mL of diethyl ether. The combined extracts were dried over anhydrous sodium sulfate and evaporated in vacuo to give a clear brown liquid. This was purified by column chromatography (silica gel), eluting with 2:1 hexane-ethyl acetate to afford 12.5 g of the title product. $^1$H NMR: $\delta$ (CDCl$_3$) 7.2–7.45 (5H, m), 6.06–6.13 (1H, m), 4.25–4.28 (2H, d), 1.92 (3H, s), 1.76 (1H, br.s). $^{13}$C NMR: $\delta$ (CDCl$_3$) 17.62, 59.2, 60.5, 87.7, 91.5, 120.85, 123.2, 128.1, 128.3, 131.56, 135.59.

(b) N-(trans-3-methyl 5-phenyl-2-penten-4-ynyl)-oxyphthalimide

Diethyl azodicarboxylate (15.2 mL, 76 mmol) was added dropwise to a solution of N-hydroxyphthalimide (11.2 g, 69 mmol), trans-3-methyl-5-phenyl-2-penten-4-yn-1-ol (11.83 g, 69 mmol), and triphenylphosphine (18.03 g, 69 mmol) in 500 mL of tetrahydrofuran at room temperature. After stirring at room temperature for 16 hours, the reaction mixture was evaporated in vacuo to give a yellow solid. The solid was purified by column chromatography (silica gel), eluting with dichloromethane to give a yellow solid that was recrystalized from ethanol to 12.29 g of the title product, m.p. 96°–98° C.

(c) O-(Trans-3-methyl-5-phenyl-2-penten-4-ynyl)hydroxylamine hydrochloride

Methylhydrazine (1 mL, 18.8 mmol) was added dropwise to a solution of N-(trans-3-methyl-5-phenyl-2-penten-4-ynyl)oxyphthalimide (5.96 g, 18.8 mmol) in 20 mL of dichloromethane. A precipitate formed immediately. The reaction was stirred for 2.5 hours, then filtered. The filtrate was diluted to 500 mL with diethyl ether and anhydrous hydrogen chloride gas was bubbled into the dilute solution to give a precipitate of the title product, 4.04 g, m.p. 196°–197° C.

II. O-(3-Methyl-2-butenyl)hydroxylamine hydrochloride (a) N-(3-Methyl-2-butenyl)oxyphthalimide Potassium carbonate (7.55 g, 54.6 mmol) was added to a solution of N-hydroxyphthalimide (13.93 g, 85.4 mmol) in 150 mL of DMSO to give a wine-red colored solution. 4-Bromo-2-methyl-2-butene (20 g, 134 mmol) was added to the solution dropwise and the reaction was stirred for 16 hours at room temperature. The reaction was poured into 600 mL of ice water to give a white crystalline solid. The crude crystalline product was filtered, washed with ice water, and air dried. The crystalline product was recrystallized from ethanol to give 15.7 g, m.p. 97°–98° C.

(b) O-(3-Methyl-2-butenyl)hydroxylamine hydrochloride

Methylhydrazine (2 mL, 37.6 mmol) was added dropwise to a cooled solution (0° C.) of N-(3-methyl-2-butenyl)oxyphthalimide (8.69 g, 37.6 mmol) in 30 mL of dichloromethane. A precipitate formed immediately. The reaction was warmed to room temperature and stirred for 2 hours. The reaction mixture was filtered and the filtrate diluted to 500 mL with diethyl ether. Anhydrous hydrogen chloride gas was bubbled into the dilute solution to a precipitate of the hydrochloride salt of the title product to give 5.2 g, m.p. 143°–145° C.

III. O-(3-(4[-Methoxyphenyl)-2-propynyl)hydroxylamine hydrochloride (a) 3-(4'-Methoxyphenyl)-2-propyn-1-ol Diethylamine (80 mL, propargyl alcohol (6.4 mL, 0.11 mol), copper(I)iodide (0.7 g), tetrahydrofuran (25 mL), and tetrakis(triphenylphosphine)palladium(o) (1.2 g) were placed in a 250-mL flask under nitrogen. A solution of p-iodoanisole (23.4 g, 0.1 mol) in 40 mL of tetrahydrofuran was added to the reaction dropwise over 30 minutes. The reaction was stirred for 16 hours at room temperature, then evaporated in vacuo to give a dark brown residue. The residue was dissolved in 200 mL of water and extracted four times with diethyl ether (200 mL). The combined extracts were dried over anhydrous sodium sulfate and evaporated to give a dark brown solid that was purified by column chromatography (silica gel), eluting with 9:1 hexane-ethyl acetate to give 15.38 g of the title product.

$^1$H NMR: $\delta$ (CDCL$_3$) 7.2–7.3 (2H, d), 6.6–6.7 (2H, d), 4.25–4.40 (2H, d), 3.65 (3H, s), 1.85–2.05 (1H, t).

(b) N-(3-(4,-Methoxyphenyl)-2-propynyl)-oxyphthalimide

Diethyl azodicarboxylate (21 mL, 104 mmol) was added dropwise to a solution of 3-(4'-methoxyphenyl)-2-propyn-1-ol (15.38 g, 94.8 mmol), N-hydroxyphthalimide (15.47 g, 94.8 mmol), and triphenylphosphine (24.9 g, 94.8 mmol), and in 500 mL of tetrahydrofuran at room temperature under nitrogen. The reaction was stirred for 24 hours, then evaporated in vacuo to give a crude solid. The crude solid was purified by column chromatography (silica gel), eluting with chloroform to give after evaporation of solvent a crystalline solid that was recrystallized from ethanol to give 20.13 g, m.p. 145°–147° C.

(c) O-(3-(4,-Methoxyohenyl)-2-propynyl)hydroxylamine hydrochloride

Methyl hydrazine (2 mL, 37.6 mmol) was added dropwise to a solution of N-(3 (4,-methoxyphenyl)-2-propynyl)oxyphthalmide (11.55 g, 37.6 mmol) in 40 mL of dichloromethane at 0° C. The reaction was warmed to room temperature and stirred for 3 hours. The reaction was filtered and the filtrate was diluted to 500 mL with diethyl ether. Anhydrous hydrogen chloride gas was bubbled into the dilute solution to give a precipitate of the hydrochloride salt of the title product, 8.21 g, m.p. 140°–142° C.

IV. O-(2,5-Hexadiynyl)hydroxylamine hydrochloride (a) 2,5-Hexadiyn-1-ol ($\pm$)-Acetaldehyde ethyl propargyl acetal (34 mL, 0.25 mol) was added to a heated (45° C.) solution of ethyl magnesium bromide (3.0M solution in diethyl ether; 90 mL, 0.27 mol) in 300 mL of dry tetrahydrofuran. After stirring for 30 minutes, copper(I)chloride (1.25 g) was added and reaction mixture heated at 50° C. for 30 minutes. Propargyl bromide (32 mL, 0.28 mol) was added to the reaction mixture dropwise while heating the reaction at 60° C. After the addition, the reaction was heated at 60° C. for 1.5 hours, then cooled to room temperature.

The reaction mixture was poured into 250 mL of aqueous solution of 5 g of KCN and 38 g of NH$_4$Cl. The layers were separated and the aqueous layer extracted three times with 200 mL of diethyl ether. The combined organic layers were washed with saturated NH₄Cl solution, dried over anhydrous Na₂SO₄, and evaporated in vacuo to give a brown oil.

The crude brown oil was dissolved in 100 mL of methanol and 1 mL of concentrated HCl and refluxed for 45 minutes. The reaction mixture was evaporated in vacuo to give a brown liquid that was dissolved in 100 mL of saturated NH₄Cl and extracted six times with 150 mL of diethyl ether. The combined extracts were dried over anhydrous Na₂SO₄ and evaporated in vacuo to give a brown liquid. This was purified by vacuum distillation (b.p. 60° C./0.2 mm Hg) to give 16.2 g of the title product. $^1$H NMR: δ (CDCl₃) 4.2 (2H, m), 3.1–3.3 (2H, m), 2.8–3.1 (1H, br.s), 2.05–2.2 (1H, m).

(b) N-(2,5-Hexadiynyl)oxyphthalimide

Diethyl azodicarboxylate (24 mL, 117 mmol) was added dropwise to a solution of N-hydroxyphthalimide (17.33 g, 106 mmol), triphenylphosphine (27.9 g, 106 mmol) and 2,5-hexadiyn-1-ol (10 g, 106 mmol) in 400 mL of tetrahydrofuran and stirred for 72 hours at room temperature. The reaction was evaporated in vacuo to give a yellow solid that was purified by column chromatography (silica gel), eluting with dichloromethane to give a light yellow solid. This was recrystallized from ethanol to give 15.3 g of the title product, m.p. 134°–135° C.

(c) O-(2,5-Hexadiynyl)hydroxylamine hydrochloride

Methyl hydrazine (2 mL, 37.6 mmol) was added dropwise to a solution of N-(2,5-hexadiynyl)oxyphthalimide (9 g, 37.6 mmol) in 75 mL of dichloromethane and stirred at room temperature for 3 hours. The reaction mixture was filtered and the filtrate diluted to 400 mL with diethyl ether. Anhydrous hydrogen chloride gas was bubbled into the dilute solution to give a precipitate of the hydrochloride salt of the title product, 3.96 g, m.p. 141°–143° C.

The compounds of the present invention are centrally acting muscarinic agents and are thus useful as analgesic agents for the treatment of pain in mammals including man, as sleep aids, and as agents for treating the symptoms of senile dementia, Alzheimer's disease, Huntington's chorea, tardive dyskinesia, hyperkinesia, mania, or similar conditions of cerebral insufficiency characterized by decreased cerebral acetylcholine production or release.

The biological activity of compounds of the present invention was evaluated using a number of tests. The activity of compounds of this invention as central muscarinic binding site agonists and antagonists was measured. In the RQNB screening assay, which is described more fully by Mark Watson, et al, *J. Pharmacol. and Exp. Ther.*, 237(2):411 (1986), rat cerebral cortex tissue was treated with radiolabeled quinuclidinyl benzilate, a known muscarinic binding site antagonist. The concentrations of test compound required to inhibit 50% of the binding of this muscarinic antagonist were then determined.

Similarly, in the RCMD screening assay, described more fully by T. W. Vickroy, et al, 229(3):747 (1984), rat cerebral cortex tissue was treated with radiolabeled cis-methyldioxolane, a known muscarinic binding site agonist. The concentrations of test compounds required to inhibit 50% of the binding of this muscarinic agonist were then determined. These values are reported as IC₅₀ concentrations in Table 2 and demonstrate that the compounds of the present invention possess significant muscarinic activity.

TABLE 4

| Example No. | IC₅₀ nM RCMD | IC₅₀ nM RQNB |
| --- | --- | --- |
| 3 | 18.2 | 24558 |
| 2 | 12.5 | 3112 |
| 4 | 3.5 | 3519 |
| 5 | 133 | 5947 |
| 6 | 120 | 3846 |
| 7 | 46 | 2030 |
| 8 | 53 | 4775 |
| 48 | 116 | 8820 |
| 49 (Isomer A) | 12.9 | 434 |
| 49 (Isomer B) | 256 | 9650 |
| 77 | 8 | 958 |
| 78 | 25 | 4680 |
| 79 | 1 | 807 |
| 80 | 12 | 4234 |
| 81 | 4 | 2063 |
| 82 | 121 | 19308 |
| 83 | 226 | 19617 |
| 84 | 320 | 11679 |
| 85 | 157 | 12632 |
| 87 | 110.1 | 13101 |
| 89 | 27.75 | 6927 |
| 90 | 147.8 | 14803 |
| 91 | 218.7 | 17658 |
| 93 | 27.86 | 4443 |
| 96 | 29.86 | 6092 |
| 98 | 12.31 | 1305 |
| 99 | 33.73 | 1934 |
| 102 | 53.16 | 6300 |
| 103 | 88.93 | 11089 |
| 104 | 28.29 | 6399 |
| 105 | 235.53 | 69540 |
| 106 | 13.55 | 2339 |
| 107 | 56.92 | 7728 |
| 108 | 16.53 | 2692 |
| 109 | 58.22 | 6998 |
| 113 | 246.2 | 12636 |
| 117 | 7.09 | 1279 |
| 118 | 113.7 | 8319 |
| 120 | 0.15 | 44 |
| 121 | 1.02 | 181 |

Similarly, in a RQNB binding assay in CHO-hm1 and CHO-hm2 cells the following data were obtained which further demonstrates the selectivity of certain compounds for the M1 receptor.

| Example No. | RQNB3m2 IC₅₀ nM | RQNB3m1 IC₅₀ nM | RQNB3m2/RQNB3m1 |
| --- | --- | --- | --- |
| 122 | 7510 | 870 | 8.69 |
| 87 | 84400 | 10600 | 7.96 |
| 89 | 52000 | 7680 | 6.80 |
| 100 | 20700 | 3340 | 6.2 |
| 102 | 24750 | 4010 | 6.2 |
| 113 | 85800 | 15360 | 5.6 |
| 93 | 20800 | 4030 | 5.2 |
| 96 | 27200 | 5460 | 5.0 |
| 95 | 47910 | 9850 | 4.86 |
| 106 | 8600 | 1800 | 4.77 |
| 67 | 25800 | 5420 | 4.76 |
| 91 | 69300 | 16600 | 4.2 |
| 98 | 4020 | 1120 | 3.6 |
| 55 | 31720 | 8840 | 3.6 |
| 105 | 44100 | 12330 | 3.58 |
| 120 | 120 | 35 | 3.43 |
| 104 | 46630 | 15120 | 3.08 |
| 103 | 38700 | 14120 | 2.74 |
| 117 | 45080 | 24580 | 1.83 |
| 125 | 32590 | 6200 | 5.24 |

In therapeutic use as agents for treating pain or for treating cerebral insufficiency, the compounds utilized in the pharmaceutical method of this invention are administered to the patient at dosage levels of from 0.07 to 700 mg per day. For a normal human adult of approximately 70 kg of body weight, this translates into a dosage of from 0.01 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act is diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can a packaged preparation, the package containing discrete quantities of the preparation, for example, packeted tablets, capsules, and powders in vials or ampoules. The unit dosage form can also be capsule, cachet, or tablet itself, or it can be the appropriate number of any of these packaged forms.

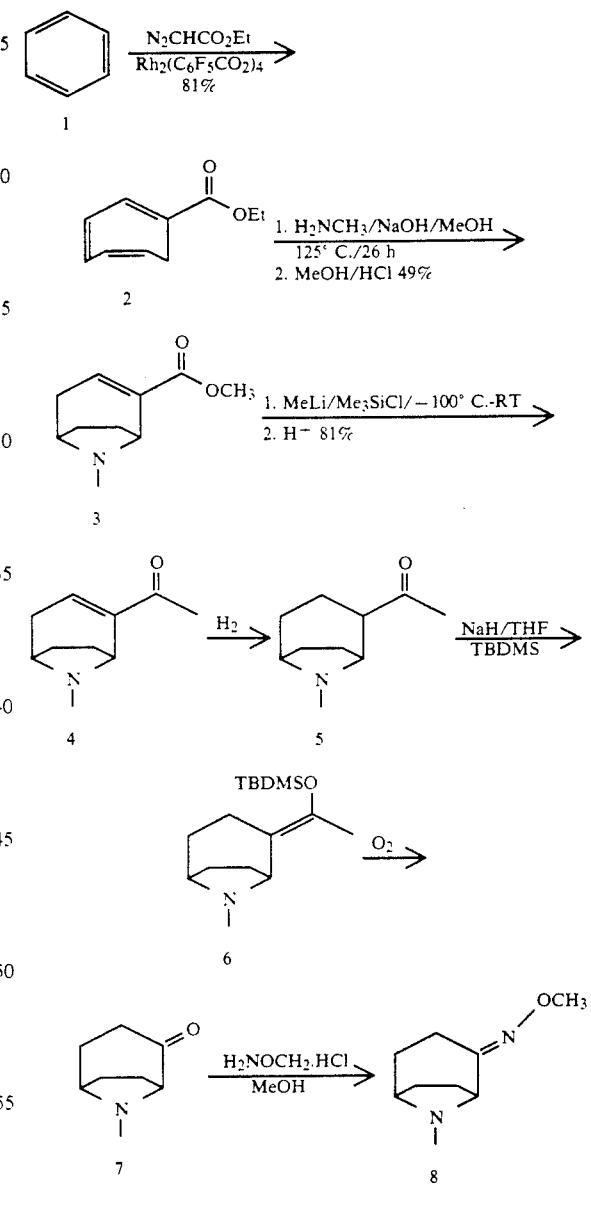

We claim:
1. A compound of the following formulas I, II, or III, its enantiomer, its geometric isomer or a pharmaceutically acceptable salt thereof:

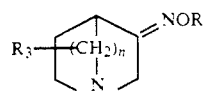

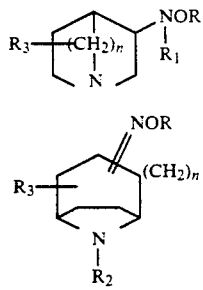

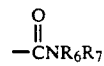

wherein n is one;
wherein each of $R_1$ and $R_2$ is hydrogen or straight or branched lower alkyl having from 1 to 4 carbon atoms;
wherein $R_3$ is hydrogen, a straight or branched lower alkyl group having from 1 to 6 carbon atoms, hydroxy, a straight or branched lower alkoxy group having from 1 to 4 carbon atoms, acyloxy group wherein the acyl moiety has from 2 to 5 carbon atoms, or the group $-(CH_2)_q-NR_{11}R_{12}$ wherein Q is zero or 1 to 4 and each of $R_{11}$ and $R_{12}$ is the same or different and is hydrogen or a straight or branched lower alkyl group having from 1 to 4 carbon atoms; or cycloalkyl having from 3 to 6 carbon atoms;
wherein R is
(a) hydrogen;
(b) a straight or branched hydrocarbon chain having from 1 to 20 carbon atoms which is saturated or which is unsaturated and contains from 1 to 4 double and/or triple bonds;
(c) phenyl or phenyl substituted with 1 to 3 substituents selected from chlorine, bromine, fluorine, trifluoromethyl, hydroxy, trifluoromethoxy, straight or branched alkoxy having from 1 to 4 carbon atoms, straight or branched alkyl having from 1 to 4 carbon atoms, nitro, $-NR_4R_5$ wherein each of $R_4$ and $R_5$ is hydrogen or a straight or branched alkyl group having from 1 to 4 carbon atoms;
(d) cycloalkyl having from 3 to 8 carbon atoms or a cycloalkenyl group having from 4 to 8 carbon atoms;
(e) a straight or branched hydrocarbon chain having from 1 to 20 carbon atoms which is saturated or which is unsaturated and contains from 1 to 4 double and/or triple bonds, and the terminal carbon of the hydrocarbon chain is substituted with a group selected from:
(i) A cycloalkyl group having from 3 to 8 carbon atoms or a cycloalkenyl group having from 4 to 8 carbon atoms;
(ii) an aromatic group selected from phenoxy, phenyl, 2- or 3-thienyl, 2- or 3-furanyl, 2- or 3-pyrrolyl, 2-, 3-, or 4-pyridinyl, 3- or 5-(1,2,4)-thiadiazolyl, 3-(1,2,5)-thiadiazolyl, 2-(1,3,4)-thiadiazolyl, 2-triazinyl, 3-or 5-(1,2,4)-oxadiazolyl, 2-(1,3,4)-oxadiazolyl, 3-(1,2,5)-oxadiazolyl, 3- or 5-thiadiazolyl, 2-or 5-pyrimidinyl, 3-or 4-pyridazinyl, 2-, 4-, or 5-thiazolyl, 2-, 4-, or 5-oxazolyl, or 2-pyrazinyl wherein the aromatic group is unsubstituted or is substituted with 1 or 2 substituents selected from straight or branched alkyl having from 1 to 4 carbon atoms, straight or branched alkoxy having from 1 to 4 carbon atoms, chlorine, fluorine, bromine, trifluoromethyl, nitro, hydroxy, trifluoromethoxy, or $NR_4R_5$ wherein $R_4$ and $R_5$ have the meanings defined above,
(iii) $-NR_6R_7$ wherein each of $R_6$ and $R_7$ is hydrogen, alkyl having from 1 to 4 carbon atoms, phenyl or benzyl, or $-NR_6R_7$ taken together form a pyrrolidino, piperidino, piperazino, or morpholino ring;
(iv)

wherein $R_6$ and $R_7$ have the meanings defined above;
(v)

$$-\overset{O}{\underset{\|}{C}}R_8$$

wherein $R_8$ is a straight or branched alkyl group having from 1 to 6 carbon atoms;
(vi) CN;
(vii) $-CO_2R_9$ wherein $R_9$ is hydrogen, a straight or branched hydrocarbon group having from 1 to 6 carbon atoms which is saturated or which is unsaturated and contains 1 or 2 double and/or triple bonds, or benzyl;
(viii) $XR_{10}$ wherein X is oxygen or sulfur, and $R_{10}$ is a straight or branched hydrocarbon chain having from 1 to 6 carbon atoms which is saturated or which is unsaturated and contains 1 or 2 double and/or triple bonds and is unsubstituted or is substituted with an alkoxy group having from 1 to 4 carbon atoms.
(ix) biphenylyl;
(f) the group $-CH_2CH_2CH=C(Ph)_2$; or
(g) the group

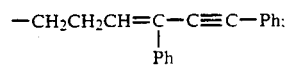

with the proviso that the following compounds are excluded: compounds of Formula III wherein R is hydrogen.

2. A compound of claim 1 having the formula

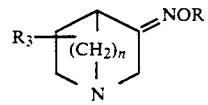

wherein n, $R_3$, and R have the meanings defined in claim 1.

3. A compound of claim 2 wherein R is a straight or branched hydrocarbon chain having from 1 to 20 carbon atoms and which is saturated or which is unsaturated and contains from 1 to 4 double and/or triple bonds.

4. A compound of claim 3 which is
1-Azabicyclo heptan-3-one, O-ethyloxime;
1-Azabicyclo heptan-3-one, O-methyloxime;
1-Azabicyclo heptan-3-one, O-2-propynyloxime;
1-Azabicyclo heptan-3-one, O-propyloxime;
1-Azabicyclo heptan-3-one, O-(1-methylethyl)oxime;
1-Azabicyclo heptan-3-one, O-(2-propenyl)oxime;

1-Azabicyclo heptan-3-one, O-(1-methyl-2-propenyl)oxime;
1-Azabicyclo heptan-3-one, O-(3-butenyl)oxime;
1-Azabicyclo heptan-3-one, O-(tert-butyl)oxime;
1-Azabicyclo heptan-3-one, O-(2-butynyl)oxime;
1-Azabicyclo heptan-3-one, O-(1-methyl-2-butynyl)oxime;
1-Azabicyclo heptan-3-one, O-(1-methyl-2-propynyl)oxime;
1-Azabicyclo heptan-3-one, O-(E-2-penten-4-ynyl)oxime;
1-Azabicyclo heptan-3-one, O-(Z-2-penten-4-ynyl)oxime;
1-Azabicyclo heptan-3-one, O-(2-pentyn 4-enyl)oxime;
1-Azabicyclo heptan-3-one, O-(2,4-pentadiynyl)oxime;
1-Azabicyclo heptan-3-one, O-(1-ethynylpropynyl)oxime;
1-Azabicyclo heptan-3-one, O-(2,4-pentadienyl)oxime;
1-Azabicyclo heptan-3-one, O-(2,4-hexadienyl)oxime;
1-Azabicyclo heptan-3-one, O-(Z-2-butenyl)oxime;
1-Azabicyclo heptan-3-one, O-(E-2-butenyl)oxime;
1-Azabicyclo heptan-3-one, O-(2,5-hexadiynyl)oxime;
1-Azabicyclo heptan-3-one, O-(2-penten-4-ynyl)oxime;
1-Azabicyclo heptan-3-one, O-(2-pentynyl)oxime;
Z-(±)-1-Azabicyclo heptan-3-one, O-2-propenyloxime;
E-(±)-1-Azabicyclo heptan-3-one, O-2-propenyloxime;
Z-(±)-1-Azabicyclo heptan-3-one, O-2-propynyloxime;
Z-(±)-1-Azabicyclo heptan-3-one, O-(2 methyl 2-propenyl)oxime;
E-(±)-1-Azabicycloheptan-3 one, O-(2 methyl-2 propenyl)oxime;
Z-(±)-1-Azabicyclo heptan-3 one, O-4-pentynyloxime;
E-(±)-1-Azabicyclo heptan-3 one, O-4-pentynyloxime;
Z-(±)-1-Azabicyclo heptan-3-one, O-3-pentynyloxime;
E-(±)-1-Azabicyclo heptan-3-one, O-3-pentynyloxime;
Z-(±)-1-Azabicyclo heptan-3-one, O-(2,5-heptadiynyl)oxime;
E-(±)-1-Azabicyclo heptan-3-one, O-) (2,5-heptadiynyl)oxime;
Z-(±)-1-Azabicyclo heptan-3-one, O-(2-hexyn-5-enyl)oxime;
Z-(±)-1-Azabicyclo heptan-3-one, O-(4-methyl 2-pentyn-4-enyl)oxime;
E-(±)-1-Azabicyclo heptan-3-one, O-(4-methylpentyn-4-enyl)oxime;
Z-(±)-1-Azabicyclo heptan-3-one, O-(2-hexynyl)oxime;
E-(±)-1-Azabicyclo heptan-3-one, O-(2-hexynyl)oxime;
Z-(±)-1-Azabicyclo heptan-3-one, O-(2-heptynyl)oxime;
E-(±)-1 Azabicyclo heptan-3-one, O-(2-heptynyl)oxime;
(Z)-(±)-1-Azabicyclo heptan-3-one, O-(2,5,8-nonatriynyl)oxime;
(E)-(±)-1-Azabicyclo heptan-3-one, O-(2,5,8 nonatriynyl)oxime;
Z-(±)-1-Azabicyclo heptan-3-one, O-(Z-3 methyl-2-penten-4-ynyl)oxime;
E-(±)-I-Azabicyclo heptan-3-one, O-(Z-3-methyl-2-penten-4-ynyl)oxime;
Z-(±)-I-Azabicyclo heptan-3-one, O-(E-3-methyl-2-penten-4-ynyl)oxime;
E-(±)-1-Azabicyclo heptan-3-one, O-(E-3-methyl-2-penten-4-ynyl)oxime;
Z-(±)-1-Azabicyclo heptan-3-one, O-(4-methyl 2 pentynyl)oxime;
E-(±)-1-Azabicyclo heptan 3-one, O-(4-methyl-2-pentynyl)oxime;
Z-(±)-1-Azabicyclo heptan-3-one, O-(4,4-dimethyl-2 pentynyl)oxime;
E-(±)-1-Azabicyclo heptan-3 one, O-(4,4-dimethyl-2-pentynyl)oxime;
Z-(±)-1-Azabicyclo heptan-3-one, O-(3-methyl-2-butenyl)oxime;
E-(±)-1-Azabicyclo heptan-3-one, O-(3-methyl-2-butenyl)oxime; and
Z-(±)-1-Azabicyclo heptan-3-one, O-(3,7-dimethyl-2,6-octadienyl)oxime; or a pharmaceutically acceptable salt thereof.

5. A pharmaceutically acceptable salt of a compound of claim 4 wherein the salt is a hydrochloride or an oxalate.

6. A compound of claim 2 wherein R is a straight or branched hydrocarbon chain having from 1 to 20 carbon atoms which is saturated or which is unsaturated and contains from 1 to 4 double and/or triple bonds, and the terminal carbon of the hydrocarbon chain is substituted.

7. A compound of claim 6 wherein the terminal carbon of the hydrocarbon chain is substituted with an aromatic group selected from phenoxy, phenyl, 2-or 3-thienyl, 2- or 3-furanyl, 2- or 3-pyrrolyl, 2-, 3-, or 4-pyridinyl wherein the aromatic group is unsubstituted or is substituted with 1 to 3 substituents selected from a straight or branched alkyl group having from 1 to 4 carbon atoms, a straight or branched alkoxy group having from 1 to 4 carbon atoms, chlorine, fluorine, bromine, trifluoromethyl, nitro, hydroxy, trifluoromethoxy, or $NR_4R_5$ wherein each of $R_4$ and $R_5$ is hydrogen or a straight or branched alkyl group having from 1 to 4 carbon atoms.

8. A compound of claim 7 which is
1-Azabicyclo heptan-3-one, O-(2-thienylmethyl)oxime;
1-Azabicyclo heptan-3-one, O-(2-furylmethyl)oxime;
Z-(±)-1-Azabicyclo heptan-3 one, O-(3-thienylmethyl)oxime;
Z-(±)-1-Azabicyclo heptan-3-one, O-(3-phenyl-2-propynyl)oxime;
E-(±)-1-Azabicyclo heptan-3-one, O-(3-phenyl-2-propynyl)oxime;
Z-(±)-1-Azabicyclo heptan-3-one, O-(3-(4'-methoxyphenyl)-2-propynyl)oxime;
E-(±)-1-Azabicyclo heptan 3-one, O-(3-(4'-methoxyphenyl)-2-propynyl)oxime;
Z-(±)-1-Azabicyclo heptan-3-one, O-(3-(3'-methoxyphenyl)-2-propynyl)oxime;
E-(±)-1-Azabicyclo heptan-3-one, O-(3-(3'-methoxyphenyl)-2-propynyl)oxime;
Z-(±)-1-Azabicyclo heptan-3-one, O-(3-(2'-methoxyphenyl)-2-propynyl)oxime;
E-(±)-1-Azabicyclo heptan-3-one, O-(3-(2'-methoxyphenyl)-2-propynyl)oxime;
Z-(±)-1-Azabicyclo heptan-3-one, O-(3-(2'-fluorophenyl)-2-propynyl)oxime;
E-(±)-1-Azabicyclo heptan-3-one, O-(3-(2'-fluorophenyl)-2-propynyl)oxime;
Z-(±) 1-Azabicyclo heptan-3-one, O-(3-(3'-fluorophenyl)-2-propynyl)oxime;
Z-(±)-1-Azabicyclo heptan 3-one, O-(3 (4'-fluorophenyl)-2-propynyl)oxime;
E-(±)-1-Azabicyclo heptan-3-one, O-(3-(4'-fluorophenyl)-2-propynyl)oxime;
Z-(±)-1-Azabicyclo heptan-3-one, O-(3-(2'-chlorophenyl)-2-propynyl)oxime;

E-(±)-1-Azabicyclo heptan-3-one, O-(3-(2'-chlorophenyl)-2-propynyl)oxime;
Z-(±)-1-Azabicyclo heptan-3-one, O-(3-(3'-chlorophenyl)-2-propynyl)oxime;
E-(±)-1-Azabicyclo heptan-3-one, O-(3-(3'-chlorophenyl)-2-propynyl)oxime;
Z-(±)-1-Azabicyclo heptan-3-one, O-(3-(4'-chlorophenyl)-2-propynyl)oxime;
Z-(±)-1-Azabicyclo heptan-3-one, O-(3-(4,-methylphenyl)-2-propynyl)oxime;
Z-(±)-1-Azabicyclo heptan 3-one, O-(3-(3'-nitrophenyl)-2-propynyl)oxime;
E-(±)-1-Azabicyclo heptan-3-one, O-(3-(3'-nitrophenyl)-2-propynyl)oxime;
Z-(±)-1-Azabicyclo heptan-3-one, O-(3-(2-thienyl)-2-propynyl)oxime;
E-(±)-1-Azabicyclo heptan-3 one, O-(3-(2-thienyl)-2-propynyl oxime;
Z-(±)-1-Azabicyclo heptan-3-one, O-(3-(3-thienyl)-2-propynyl)oxime;
E-(±)-1-Azabicyclo heptan-3-one, O-(3-(3-thienyl)-2-propynyl)oxime;
Z-(±)-1-Azabicyclo heptan-3-one, O-(3-(3-pyridinyl)-2-propynyl)oxime;
Z-(±)-1-Azabicyclo heptan-3-one, O-(2-phenylethyl)oxime;
E-(±)-1-Azabicyclo heptan-3-one, O-(2-phenylethyl)oxime;
Z-(±)-1-Azabicyclo heptan-3-one, O-(2-phenoxyethyl)oxime;
E-(±)-1-Azabicyclo heptan-3-one, O-(2-phenoxyethyl)oxime;
Z-(±)-1-Azabicyclo heptan-3-one, O-(3-phenylpropyl)oxime;
E-(±)-1-Azabicyclo heptan-3-one, O-(3-phenylpropyl)oxime;
Z-(±)-1-Azabicyclo heptan-3-one, O-(Z-3-methyl-5-phenyl-2-penten-4-ynyl)oxime;
E-(±)-1-Azabicyclo heptan-3-one, O-(Z-3-methyl-5-phenyl-2-penten 4-ynyl)oxime;
Z-(±)-1-Azabicyclo heptan-3 one, O-(E-3-methyl-5-phenyl-2 penten-4-ynyl)oxime; and
E-(±)-1-Azabicyclo heptan-3-one, O-(E-3-methyl-5-phenyl-2-penten-4-ynyl)oxime; or a pharmaceutically acceptable salt thereof.

9. A compound of claim 8 wherein the salt is an oxalate or a hydrochloride.

10. A compound of claim 6 wherein the terminal carbon atom of the hydrocarbon chain is substituted with a —CO₂R₉ group wherein R₉ is hydrogen, a straight or branched hydrocarbon group having from 1 to 6 carbon atoms which is saturated or which is unsaturated and contains 1 or 2 double and/or triple bonds, or benzyl.

11. A compound of claim 10 which is
acetic acid, ethyl ester;
acetic acid, 2-propynyl ester; and
4-2-butenoic acid, methyl ester; or a pharmaceutically acceptable salt thereof.

12. A compound of claim 6 wherein the terminal carbon of the hydrocarbon chain is substituted with a

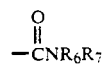
—CNR₆R₇ group wherein each of R₆ and R₇ is hydrogen, a straight or branched alkyl group having from 1 to 4 carbon atoms, phenyl, benzyl, or NR₆R₇ taken together form a pyrrolidino, piperidino, piperazino, or morpholino ring.

13. A compound of claim 12 which is
2-N-methyl acetamide;
2-N-ethyl acetamide;
2-N,N-dimethyl acetamide;
2-N,N-diethyl acetamide;
2-N-phenyl acetamide;
2-N-methylphenyl acetamide; and
1-Azabrcyclo heptan-3-one, O-pharmaceutically acceptable salt thereof.

14. A compound of claim 2 which is
1-Azabicyclo heptan-3-one, O-(2-amino-ethyl)oxime;
1-Azabicyclo heptan-3-one, O-(cyclo-propylmethyl)oxime;
1-Azabicyclo heptan-3-one, O-(2-methoxyethyl)oxime;
1-Azabicyclo heptan-3-one, O-phenyloxime;
oxyacetonitrile;
1-Azabicyclo heptan-3-one, O-(4-methoxy-2-butynyl)oxime;
acetic acid methyl ester;
Z-(±)-1-Azabicyclo heptan-3-one, O-cyclobutyloxime;
E-(±)-1-Azabicyclo heptan-3-one, O-cyclobutyloxime;
Z-(±)-1-Azabicyclo heptan-3-one, O-(2-(2 propynylthio)ethyl)oxime;
E-(±)-1-Azabicyclo heptan-3-one, O-(2-(2-propynylthio)ethyl)oxime;
1-Azabicyclo heptan-3-one, O-oxime;
Z-(±)-1-Azabicyclo heptan-3-one, O-p-biphenylyloxime;
Z-(±)-1-Azabicyclo heptan-3-one, O-(cyclohex-2-enylmethyl)oxime;
E-(±)-1-Azabicyclo heptan-3-one, O-(cyclohex-2-enylmethyl)oxime;
Z-(±)-1-Azabicyclo heptan-3-one, O-oxime;
E-(±)-1-Azabicyclo heptan-3-one, O-oxime;
Z-(±)-1-Azabicyclo heptan-3-one, O-(3-cyclohexylmethyl)-2-propynyl]oxime;
E-(±)-1-Azabicyclo heptan-3-one, O-oxime;
Z-(±)-1-Azabicyclo heptan-3-one, O-oxime,
E-(±)-1-Azabicyclo heptan-3-one, O-oxime, or a pharmaceutically acceptable salt thereof.

15. A compound of claim 1 which is

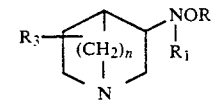

wherein n, R₃, R₁, and R have the meanings defined in claim 1.

16. A compound of claim 1 having the formula:

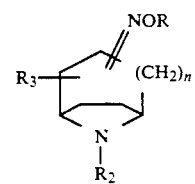

wherein n, R, R₂, and R₃ have the meanings defined in claim 1.

17. A compound of claim 16 wherein n is one.

18. A compound of claim 9 which is N-methyl-8-azabicyclo octa-3-one methyl oxime hydrochloride or N-methyl-8-azabicyclo octa-2-one methyloxime hydrochloride.

19. A pharmaceutical composition comprising the compound of claim 1 together with a pharmaceutically acceptable carrier.

20. A method of alleviating pain in a mammal which comprises administering to a mammal in need of such treatment an effective amount of a composition of claim 19.

21. A method of treating the symptoms of cognitive decline in a patient in need thereof which comprises administering to said patient an effective amount of a composition of claim 19.

* * * * *